US008318902B2

(12) United States Patent
Lynn et al.

(10) Patent No.: US 8,318,902 B2
(45) Date of Patent: Nov. 27, 2012

(54) BIOMATERIAL

(75) Inventors: Andrew Lynn, Cambridge (GB); William Bonfield, Cambridge (GB); Zachary D. Wissner-Gross, Cambridge, MA (US); Brendan A. Harley, Cambridge, MA (US); Ioannis V. Yannas, Cambridge, MA (US); Lorna J. Gibson, Cambridge, MA (US)

(73) Assignees: Cambridge Enterprise Limited, Cambridge (GB); Massachusetts Institute of Technology, Cambridge, MA (US)

( * ) Notice: Subject to any disclaimer, the term of this patent is extended or adjusted under 35 U.S.C. 154(b) by 190 days.

(21) Appl. No.: 12/377,221

(22) PCT Filed: Aug. 10, 2007

(86) PCT No.: PCT/GB2007/003046
§ 371 (c)(1),
(2), (4) Date: Oct. 26, 2009

(87) PCT Pub. No.: WO2008/017838
PCT Pub. Date: Feb. 14, 2008

(65) Prior Publication Data
US 2010/0248368 A1    Sep. 30, 2010

(30) Foreign Application Priority Data
Aug. 11, 2006  (GB) .................................. 0616026.1

(51) Int. Cl.
*A61K 38/17*      (2006.01)
(52) U.S. Cl. ........................................... 530/356
(58) Field of Classification Search ........................ None
See application file for complete search history.

(56) References Cited

U.S. PATENT DOCUMENTS

| 7,153,938 B2 | 12/2006 | Kikuchi et al. | |
| 2002/0071855 A1* | 6/2002 | Sadozai et al. | 424/426 |
| 2003/0023318 A1 | 1/2003 | Simmoteit et al. | |
| 2003/0114061 A1* | 6/2003 | Matsuda et al. | 442/123 |
| 2003/0232071 A1 | 12/2003 | Gower et al. | |

FOREIGN PATENT DOCUMENTS

| EP | 0164484 A1 | 12/1985 |
| EP | 0214070 A1 | 3/1987 |
| EP | 1566186 A | 8/2005 |
| WO | 2006034365 A2 | 3/2003 |
| WO | 2005051447 A1 | 6/2005 |
| WO | 2006095154 A2 | 9/2006 |

OTHER PUBLICATIONS

International Search Report, PCT/GB2007/003046, dated Jan. 30, 2009, 4 pages.

Written Opinion, PCT/GB2007/003046, dated Jan. 30, 2009, 7 pages.
Bakos et al, "Hydroxyapatite-Collagen-Hyaluronic Acid Composite", Biomaterials, Elsevier Science, Oxford, Great Britain, Jan. 1, 1999, pp. 191-195.
Abstract of EP0214070; Mar. 11, 1987.
Abstract of EP0164484; Dec. 18, 1985.
Damink et al., "Cross-linking of Dermal Sheep Collagen Using a Water-Soluble Carbodiimide", Biomaterials, vol. 17, No. 8, 1996, pp. 765-773.
Schloesser, Gordon, "Effects of the Degradation Rate of Collagen Matrices on Articular Chondrocyte Proliferation and Biosynthesis in Vitro", Tissue Engineering, vol. 10, No. 7/8, 2004, pp. 1287-1295.
Yannas et al."Synthesis and Characterization of a Model Extracellular Matrix That Induces Partial Regeneration of Adult Mammalian Skin", Proceedings of the National Academy of Sciences of the United States of America, vol. 86, Issue 3, Feb. 1989, pp. 933-937.
O'Brien et al., "Influence of Freezing Rate on Pore Structure in Freeze-Dried Collagen-GAG Scaffold", Biomaterials, vol. 25, No. 6, 2004, pp. 1077-1086.
Sherwood et al.,"A three-dimensional Osteochondral Composite Scaffold for Articular Cartilage Repair" Biomaterials, vol. 23, No. 24, Dec. 2002, pp. 4739-4751.
Schaefer et al., "Tissue-Engineered Composites for the Repair of Large Osteochondral Defects", Arthritis & Rheumatism, vol. 46, No. 9, Sep. 2002, pp. 2524-2534.
Schaefer et al., "In Vitro Generation of Osteochondral Composites", Biotmaterials, vol. 21, No. 24, 2000, pp. 2599-2606.
Niederauer et al., "Evaluation of Multiphase Implants for Repair of Focal Osteochondral Defects in Goats", Biomaterials, vol. 21, No. 24, 2000, pp. 2561-2574.
Hung et al., "Anatomically Shaped Osteochondral Constructs for Articular Cartilage Repair", Journal of Biomechanics, vol. 36, vol. 12, 2003, pp. 1853-1864.
Gao et al., "Repair of Osteochondral Defects with Tissue-Engineered Two-Phase Composite Material of Injectable Calcium Phosphate and Hyaluronan Sponge", Tissue Engineering, vol. 8, No. 5, 2002, pp. 827-837.
Gao et al., "Tissue-Engineered Fabrication of an Osteochondral Composite Graft Using Rat Bone Marrow-Derived Mesenchymal Stem Cells", Tissue Engineering, vol. 7, No. 4, 2001, pp. 363-371.

(Continued)

*Primary Examiner* — Suzanne M Noakes
(74) *Attorney, Agent, or Firm* — Senniger Powers LLP

(57) ABSTRACT

A process for the preparation of a composite biomaterial comprising: providing a first substantially solid component comprising one or more of collagen, a glycosaminoglycan, albumin, hyaluronan, chitosan, and synthetic polypeptides comprising a portion of the polypeptide sequence of collagen, and optionally an inorganic material, said component having at least a surface portion that is porous; providing a fluid composition comprising one or more of collagen, a glycosaminoglycan, albumin, hyaluronan, chitosan, and synthetic polypeptides comprising a portion of the polypeptide sequence of collagen, and a liquid carrier, and optionally an inorganic material; contacting said fluid composition with said porous surface portion of said first component; cooling said fluid composition to a temperature at which the liquid carrier transforms into a plurality of solid crystals or particles; removing at least some of the plurality of solid crystals or particles by sublimation and/or evaporation.

38 Claims, 3 Drawing Sheets

OTHER PUBLICATIONS

Hunziker et al., "Functional Barrier Principle for Growth-Factor-Based Articular Cartilage Repair", Osteoarthritis and Cartilage, vol. 11, No. 5, 2003, pp. 320-327.

Yannas, Ioannis V., "Tissue and Organ Regeneration in Adults", Springer-Verlag New York, Inc., 2001, pp. 110-115 and 164-185.

* cited by examiner

BIOMATERIAL

REFERENCE TO RELATED APPLICATIONS

This application is the U.S. national stage application of International Patent Application No. PCT/GB2007/003046, filed Aug. 10, 2007, and claims the benefit of Great Britain Application No. 0616026.1, filed Aug. 11, 2006, the entire disclosures of which are incorporated herein by reference.

FIELD OF THE INVENTION

The present invention relates to the field of synthetic bone materials for biomedical applications and, in particular, to layered scaffolds comprising, for example, collagen, calcium phosphate, and optionally a glycosaminoglycan for use in tissue engineering.

BACKGROUND OF THE INVENTION

Natural bone is a biocomposite of collagen, non-collagenous organic phases including glycosaminoglycans, and calcium phosphate. Its complex hierarchical structure leads to exceptional mechanical properties including high stiffness, strength, and fracture toughness, which in turn enable bones to withstand the physiological stresses to which they are subjected on a daily basis. The challenge faced by researchers in the field is to make a synthetic material that has a composition and structure that will allow natural bone growth in and around the synthetic material in the human or animal body.

It has been observed that bone will bond directly to calcium phosphates in the human body (a property referred to as bioactivity) through a bone-like apatite layer formed in the body environment. Collagen and copolymers comprising collagen and other bioorganics such as glycosaminoglycans on the other hand, are known to be optimal substrates for the attachment and proliferation of numerous cell types, including those responsible for the production and maintenance of bone in the human body.

Hydroxyapatite is the calcium phosphate most commonly used as a constituent in bone substitute materials. It is, however, a relatively insoluble material when compared to other forms of calcium phosphate materials such as brushite, tricalcium phosphate and octacalcium phosphate. The relatively low solubility of apatite can be a disadvantage when producing a biomaterial as the rate of resorption of the material in the body is particularly slow.

Calcium phosphates such as hydroxyapatite are mechanically stiff materials. However, they are relatively brittle when compared to natural bone. Collagen is a mechanically tough material, but has relatively low stiffness when compared to natural bone. Materials comprising copolymers of collagen and glycosaminoglycans are both tougher and stiffer than collagen alone, but still have relatively low stiffness when compared to natural bone.

Previous attempts to produce a synthetic bone-substitute material having improved mechanical toughness over hydroxyapatite and improved stiffness over collagen and copolymers of collagen and glycosaminoglycans include combining collagen and apatite by mechanical mixing. Such a mechanical method is described in EP-A-0164 484.

Later developments include producing a bone-replacement material comprising hydroxyapatite, collagen and chondroitin-4-sulphate by the mechanical mixing of these components. This is described in EP-A-0214070. This document further describes dehydrothermic crosslinking of the chondroitin-4-sulphate to the collagen. Materials comprising apatite, collagen and chondroitin-4-sulphate have been found to have good biocompatibility. The mechanical mixing of the apatite with the collagen, and optionally chondroitin-4-sulphate, essentially forms collagen chondroitin-4-sulphate-coated particles of apatite. It has been found that such a material, although biocompatible, produces limited in-growth of natural bone when in the human or animal body and no remodeling of the calcium phosphate phase of the synthetic material.

Previous work has developed means through which the parameters of freeze-drying protocols can be controlled to produce porous scaffolds of collagen and one or more glycosaminoglycans (GAGs). These techniques allow scaffold features such as pore size and aspect ratio to be varied in a controlled manner, parameters known to have marked effects on the healing response at sites of trauma or injury. However, for treatment of injuries involving skeletal and musculoskeletal defects, it is necessary to develop technologies to produce porous scaffolds with material compositions and mechanical characteristics that closely match those of bone, as opposed to those of unmineralised collagen-GAG scaffolds.

The applicant's earlier International patent application, PCT/GB2006/000797, filed 6 Mar. 2006, relates to materials for biomedical applications and, in particular, to porous monolithic and porous layered scaffolds comprising, for example, collagen, calcium phosphate, and optionally a glycosaminoglycan. The content of PCT/GB2006/000797 is also set out in the Annex attached hereto so as to aid a better understanding of the present invention.

SUMMARY OF THE INVENTION

Continued use and development of advanced scaffolding materials for tissue engineering applications has revealed the need for the development of layered scaffold materials. Many relevant physiological sites in the body involve interfaces between one or more tissue types. It has been noted that particular tissue types and cell types require the development of specific scaffolding structures; often the biologically active scaffold structure can vary significantly from tissue to tissue, cell to cell, and application to application [1]. Such observations suggest that for treatment of injury sites in more complicated tissues and at sites involving interfacial damage (i.e. damage to cartilage often damages the underlying bone as well, tendon and ligament injuries near the insertion point into bone or muscle), it is necessary to develop scaffolds with both gradients in scaffold structure as well as sharp interfaces in scaffold structure.

In particular, the repair of skeletal sites damaged by trauma, deformity or disease poses a specific set of challenges. Unlike defects in skin, nerve and most other tissues, skeletal defects encompass multiple, distinct tissue types (i.e. bone, cartilage, tendon and ligament), involve locations that undergo regular mechanical loading and involve traverse interfaces between mineralized to unmineralized tissues (e.g. ligament insertion points, the "tidemark" at the bone/cartilage interface).

Current scaffold fabrication technologies do not include appropriate protocols for fabricating scaffolds with sharp gradients in parameters such as physical structure, mechanical properties, or chemical composition. A limited number of recent efforts have sought to develop tissue-engineering strategies that employ porous, layered scaffolds for the treatment of injuries such as articular joint defects involving either cartilage alone or both bone and cartilage. These constructs seek to induce the regeneration of bone and cartilage concurrently, but using separate scaffolds for each [2-9].

Despite the promise of this new approach, two major shortcomings may limit the effectiveness of the layered scaffolds reported to date. The first relates to the materials used for the respective layers of the scaffold. Resorbable synthetic polymers have been the only material used for the cartilaginous layer, and have often been a component of the osseous portion in many of these scaffolds as well. Although easy to fabricate, synthetic polymers are known to be less conducive to cell attachment and proliferation than natural polymers such as collagen, and can release high concentrations of potentially cytotoxic acids as they degrade. Moreover, for applications where tendon or ligament repair is necessary, resorbable synthetic polymers-regardless of the manner in which they are crosslinked—have inadequate strength and stiffness to withstand even the reduced load applied during rehabilitation exercises.

The second shortcoming of present layered scaffolds relates to the interface between the respective layers. In vivo, a continuity of collagen fibrils is observed across the interfaces between many tissues such as natural articular joints and tendon/ligament insertion points. The resultant system of smooth transitions (soft interfaces) imparts an intrinsic mechanical stability to these sites, allowing them to withstand physiological loading without mechanical failure. In contrast, the majority of existing layered scaffolds contain hard interfaces, forming a distinct boundary between two dissimilar materials. Suturing [7], fibrin adhesive bonding [3] and other techniques [4,5] have been used to strengthen this interface, however, interfacial debonding has still been reported even in controlled animal models. It is also worthy to note that these suturing and bonding methods are delicate, and poorly reproducible, and may thus not be practical in the clinical environment.

It is clear that novel technologies are required to further expand the ability to produce layered scaffold structures with defined, non-uniform characteristics for a multitude of applications. Of primary concern is developing appropriate technologies to produce a layered scaffold structure with appropriate interlayer bonding. This is an especially significant problem for scaffolds to be used in areas under significant mechanically loading, thereby increasing the chance of interlayer delamination.

It is of further critical importance to develop techniques to fabricate layered, porous collagen-based scaffolds. Collagen-based scaffolds have been successfully utilized as analogs of the natural extracellular matrix for a multitude of different tissue engineering studies; collagen-based scaffolds are traditionally fabricated via freeze-drying. A suspension of collagen, other applicable proteins, and a liquid carrier is solidified under appropriate thermal conditions, resulting in an interpenetrating network of ice crystals surrounded by collagen fibers. The frozen suspension is then sublimated, removing the frozen liquid carrier and leaving behind the porous scaffold structure. The dimensions of the scaffold pores are defined by the freezing process of the slurry. A significant advantage of this fabrication technique is that a continuity of collagen fibers is observed throughout the scaffold. However, to fabricate layered scaffolds with large differences in pore size and shape requires very careful control of the thermal environment. Additionally, producing scaffolds with significantly dissimilar properties such as chemical composition, crosslinking density, and material properties becomes very difficult when trying to form all structures concurrently during a single solidification step due to suspension intermixing.

The present invention extends the work described in PCT/GB2006/000797 and aims to address some of the problems associated with the prior art.

Accordingly, the present invention provides a process for the preparation of a composite biomaterial comprising:
providing a first substantially solid component comprising one or more of collagen, a glycosaminoglycan, albumin, hyaluronan, chitosan, and synthetic polypeptides comprising a portion of the polypeptide sequence of collagen, and optionally an inorganic material, said component having at least a surface portion that is porous;
providing a fluid composition comprising one or more of collagen, a glycosaminoglycan, albumin, hyaluronan, chitosan, and synthetic polypeptides comprising a portion of the polypeptide sequence of collagen, and a liquid carrier, and optionally an inorganic material;
contacting said fluid composition with said porous surface portion of said first component;
cooling said fluid composition to a temperature at which the liquid carrier transforms into a plurality of solid crystals or particles;
removing at least some of the plurality of solid crystals or particles by sublimation and/or evaporation.

The process may further comprise:
providing a second substantially solid component comprising one or more of collagen, a glycosaminoglycan, albumin, hyaluronan, chitosan, and synthetic polypeptides comprising a portion of the polypeptide sequence of collagen, and optionally an inorganic material, said component having at least a surface portion that is porous;
interposing said fluid composition between said first and second components so that it contacts with said porous surface portions;
cooling said fluid composition between said first and second components to a temperature at which the liquid carrier transforms into a plurality of solid crystals or particles;
removing at least some of the plurality of solid crystals or particles by sublimation and/or evaporation, to result in an intermediate layer between the first and second components.

DETAILED DESCRIPTION OF PREFERRED EMBODIMENTS

Figure 1:
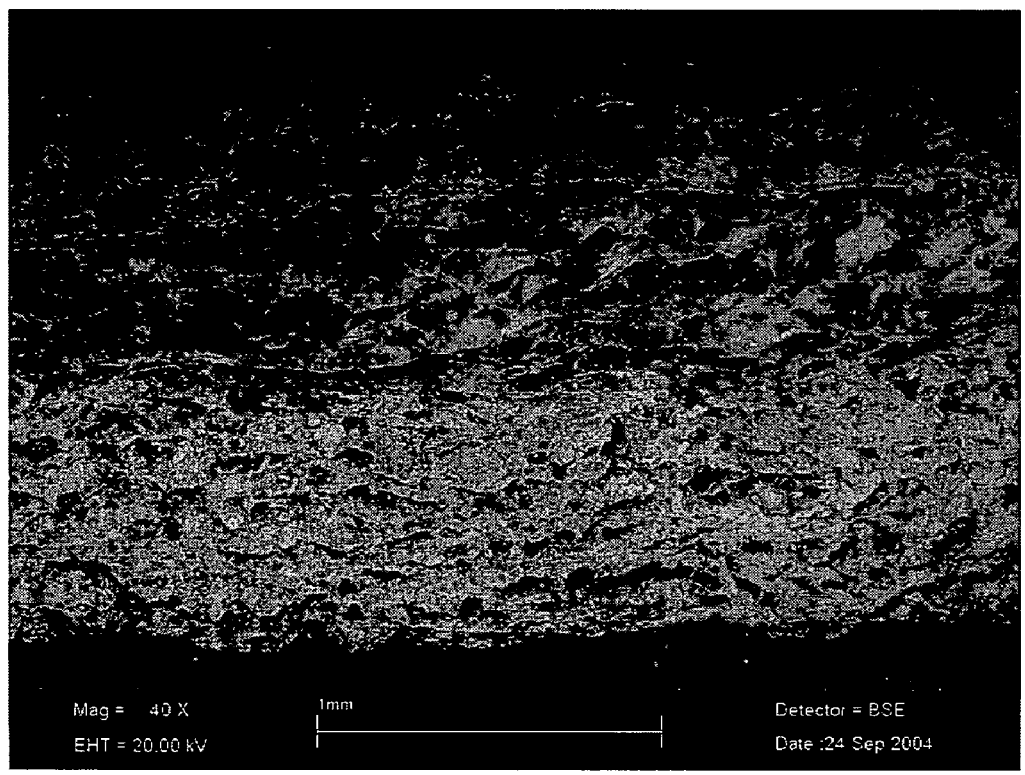
FIG. 1 shows a two-component scaffold fabricated by solid phase co-synthesis to form bilayer scaffold in accordance with Example 1C.

The term biomaterial as used herein means a material that is biocompatible with a human or animal body.

The term slurry as used herein encompasses slurries, solutions, suspensions, colloids and dispersions.

The term collagen as used herein encompasses recombinant human (rh) collagen.

The term component as used herein refers to a distinct region of, for example, a scaffold with specific chemical, structural and/or material properties. The term scaffold refers to the final, multi-component scaffold structure.

The terms composite scaffold and layered scaffold are synonymous, and refer to scaffolds comprising two or more layers, with the material composition of each layer typically differing substantially from the material composition of its adjacent layer or layers. The term single-layered scaffold or monolithic scaffold are synonymous, and refer to scaffolds comprising one layer only, with the material composition within each layer being largely homogeneous throughout.

The term porous as used herein means that the material may contain macropores and/or micropores. The pores may be on the surface and may extend into the bulk of the material. Macroporosity typically refers to features associated with pores on the scale of greater than approximately 10 microns. Microporosity typically refers to features associated with pores on the scale of less than approximately 10 microns. It will be appreciated that there can be any combination of open and closed cells within the material. For example, the material will generally contain both macropores and micropores. The macroporosity is generally open-celled, although there may be a closed cell component.

The method according to the present invention comprises a sequence of steps that can be applied in any number of repetitions in order to produce a porous composite/layered scaffold comprising a series of individual components. These individual components can be fabricated separately from one another and then joined together using any number of repetitions of the co-synthesis processes to form a single composite/layered scaffold with regions of different structural, mechanical, and/or compositional characteristics (e.g. pore size, relative density, pore shape, stiffness, chemical composition, crosslinking density, degradation rate).

After assembly of the larger composite/layered scaffold structure, any number of post-fabrication processing steps can be utilized including physical crosslinking techniques (e.g. dehydrothermal crosslinking, ultraviolet crosslinking), chemical crosslinking techniques (e.g. carbodiimide-based crosslinking, gluteraldehyde-based crosslinking) or partial degradation of the scaffold using enzyme cocktails (e.g. collagenase, dispase). Following the use of any treatments that involve hydration of the scaffold, the liquid component can be removed using, for example, a freeze-drying process.

The present invention preferably enables the production of continuous (soft) interfaces with a continuity of, for example, collagen fibrils between scaffold component layers that mimic those seen in vivo. The inventors have found that this addresses the problems related to suturing or gluing dissimilar phases together after fabrication.

The process according to the present invention offers the advantage that the individual scaffold components need not be formed at substantially the same time from the liquid state. This is in contrast to a liquid-phase co-synthesis, where all slurries are layered and solidified together.

The first component and second component (if present) is/are provided in solid or essentially solid form.

The first component and/or the second component will typically comprise(s) collagen and optionally a glycosaminoglycan.

The first component and/or the second component will typically comprise(s) an inorganic material such as a calcium phosphate material. Examples include one or more of brushite, octacalcium phosphate and apatite.

Apatite is a class of minerals comprising calcium and phosphate and has the general formula: $Ca_5(PO_4)_3(X)$, wherein X may be an ion that is typically $OH^-$, $F^-$ and $Cl^-$, as well as other ions known to those skilled in the art. The term apatite also includes substituted apatites such as silicon-substituted apatites. The term apatite includes hydroxyapatite, which is a specific example of an apatite. The hydroxyapatite may also be substituted with other species such as, for example, silicon.

In one preferred aspect of the present invention, the first component and/or the second component is/are formed from a co-precipitate of collagen and a calcium phosphate material. In another preferred aspect of the present invention, the first component and/or the second component is/are formed from a co-precipitate of collagen and a glycosaminoglycan.

Advantageously, the first component and/or the second component is/are formed from a triple co-precipitate of collagen, a calcium phosphate material and a glycosaminoglycan.

In a preferred embodiment, the first component comprises collagen and a glycosaminoglycan and optionally a calcium phosphate material, and the second component (if present) comprises collagen, a glycosaminoglycan and a calcium phosphate material.

The fluid composition will typically comprise collagen and optionally a glycosaminoglycan.

The fluid composition may further contain an inorganic material such as a calcium phosphate material. Examples include one or more of brushite, octacalcium phosphate and apatite.

The liquid carrier preferably comprises water.

The fluid composition may be provided in the form of a suspension, for example a collagen-based suspension or slurry. The suspension/slurry may further contain one or both of a glycosaminoglycan and/or a calcium phosphate material.

Preferably, the fluid composition is a suspension/slurry comprising a co-precipitate of collagen and a glycosaminoglycan and/or a triple co-precipitate of collagen, a calcium phosphate material and a glycosaminoglycan.

Alternatively, the slurry may simply comprise a mechanical mixture of collagen and the calcium phosphate material and optionally the glycosaminoglycan. This may be produced by a conventional technique such as described in, for example, EP-A-0164 484 and EP-A-0214070.

The calcium phosphate material may be selected, for example, from one or more of brushite, octacalcium phosphate and/or apatite. The calcium phosphate material preferably comprises brushite.

The pH of the suspension/slurry is preferably from 2.5 to 6.5, more preferably from 2.5 to 5.5, still more preferably from 3.0 to 4.5, and still more preferably from 3.8 to 4.2.

The suspension/slurry composition may comprise one or more glycosaminoglycans. The slurry composition may comprise one or more calcium phosphate materials.

The presence of other species (e.g. silver, silicon, silica, table salt, sugar, etc) in the suspension/slurry is not precluded.

It will be appreciated that other components may be present in the suspension/slurry. For example, growth factors, genes, drugs or other biologically active species may optionally be added, alone or in combination, to the suspension/slurry.

At least some of the plurality of solid crystals or particles may be removed by sublimation and/or evaporation to result in an intermediate layer between the first and second components. The preferred method is sublimation.

In a preferred embodiment, the process for the preparation of the composite biomaterial according to the present invention comprises:
  (a) providing a first substantially solid component comprising one or more of collagen (including recombinant human (rh) collagen), a glycosaminoglycan, albumin, hyaluronan, chitosan, and synthetic polypeptides comprising a portion of the polypeptide sequence of collagen, and optionally an inorganic material, said component having at least a surface portion that is porous;

(b) providing a second substantially solid component comprising one or more of collagen (including recombinant human (rh) collagen), a glycosaminoglycan, albumin, hyaluronan, chitosan, and synthetic polypeptides comprising a portion of the polypeptide sequence of collagen, and optionally an inorganic material, said component having at least a surface portion that is porous;

(c) providing a fluid composition comprising one or more of collagen (including recombinant human (rh) collagen), a glycosaminoglycan, albumin, hyaluronan, chitosan, and synthetic polypeptides comprising a portion of the polypeptide sequence of collagen, and a liquid carrier, and optionally an inorganic material;

(d) interposing said fluid composition between said first and second components so that it contacts with said porous surface portions;

(e) cooling said fluid composition between said first and second components to a temperature at which the liquid carrier transforms into a plurality of solid crystals or particles;

(f) removing at least some of the plurality of solid crystals or particles by sublimation and/or evaporation, to result in an intermediate layer between the first and second components.

In the present invention, a thin layer of, for example, a collagen-based suspension is advantageously placed between first and second components (eg scaffolds) and allowed to absorb into the first few layers of pores in each scaffold. The scaffold is then freeze-dried a second time, resulting in an interpenetrating network of collagen fibers between each distinct scaffold component. This process may, of course, be repeated multiple times if desired.

The chemical and physical (eg viscosity) of the suspension/slurry may be chosen depending on the chemical and physical nature of the first and second components. For example, if the pores in the first and second components are very small, then a less viscous suspension/slurry may be chosen to ensure penetration into the pores.

The steps of cooling the fluid composition to a temperature at which the liquid carrier transforms into a plurality of solid crystals or particles, and removing at least some of the plurality of solid crystals or particles by sublimation and/or evaporation may be effected by a freeze-drying technique.

If the liquid carrier is water, then the sublimation step comprises reducing the pressure in the environment around the mould and frozen suspension/slurry to below the triple point of the water/ice/water vapour system, followed by elevation of the temperature to greater than the temperature of the solid-vapor transition temperature at the achieved vacuum pressure. The ice in the product is directly converted into vapor via sublimation as long as the ambient partial liquid vapor pressure is lower than the partial pressure of the frozen liquid at its current temperature. The temperature is typically elevated to at or above 0° C. This step is performed to remove the ice crystals from the frozen suspension/slurry via sublimation.

The freeze-drying parameters may be adjusted to control pore size and aspect ratio as desired. In general, slower cooling rates and higher final freezing temperatures (for example, cooling at approximately 0.25° C. per minute to a temperature of about −10° C.) favour large pores with higher aspect ratios, while faster cooling rates and lower final freezing temperatures (for example, cooling at approximately 2.5° C. per minute to a temperature of about −40° C.) favours the formation of small equiaxed pores.

The process of the present invention may be conducted in a mould, which term is intended to encompass any mould, container or substrate capable of shaping, holding or supporting the first and second components and fluid composition. Thus, the mould in its simplest form could simply comprise a supporting surface. The mould may be any desired shape, and may be fabricated from any suitable material including polymers (such as polysulphone, polypropylene, polyethylene), metals (such as stainless steel, titanium, cobalt chrome), ceramics (such as alumina, zirconia), glass ceramics, and glasses (such as borosilicate glass).

The composition of the first component will generally not be the same as the composition of the second component.

The composition of the fluid component will generally not be the same as the composition of the first component or the second component (if present).

The composite biomaterial made by the process according to the present invention may be used to fabricate a multi-layered scaffold in which at least two layers are porous. Preferably all of the multiple layers contain collagen and preferably also a glycosaminoglycan. At least one of the layers preferably further contains a calcium phosphate material.

The first and/or second components may be prepared by the methods described in the applicant's earlier International application, PCT/GB2006/000797, filed 6 Mar. 2006, the content of which is set out in the Annex attached hereto. Moreover, the fluid composition may be that as described in PCT/GB2006/000797 in respect of the slurry compositions.

The applicant's earlier published application, PCT/GB04/004550, filed 28 Oct. 2004, describes a triple co-precipitate of collagen, brushite and a glycosaminoglycan and a process for its preparation. The content of PCT/GB04/004550 is incorporated herein by reference. The process described in PCT/GB04/004550 involves: providing an acidic aqueous solution comprising collagen, a calcium source and a phosphorous source and a glycosaminoglycan; and precipitating the collagen, the brushite and the glycosaminoglycan together from the aqueous solution to form a triple co-precipitate. The term co-precipitate means precipitation of the two or three compounds where the compounds have been precipitated at substantially the same time from the same solution/dispersion. It is to be distinguished from a material formed from the mechanical mixing of the components, particularly where these components have been precipitated separately, for instance in different solutions. The microstructure of a co-precipitate is substantially different from a material formed from the mechanical mixing of its components.

In the process for preparing the co-precipitate, the calcium source is preferably selected from one or more of calcium nitrate, calcium acetate, calcium chloride, calcium carbonate, calcium alkoxide, calcium hydroxide, calcium silicate, calcium sulphate, calcium gluconate and the calcium salt of heparin. A calcium salt of heparin may be derived from the porcine intestinal mucosa. Suitable calcium salts are commercially available, for example, from Sigma-Aldrich Inc. The phosphorus source is preferably selected from one or more of ammonium-dihydrogen phosphate, diammonium hydrogen phosphate, phosphoric acid, disodium hydrogen orthophosphate 2-hydrate ($Na_2HPO_4.2H_2O$, sometimes termed GPR Sorensen's salt) and trimethyl phosphate, alkali metal salts (eg Na or K) of phosphate, alkaline earth salts (eg Mg or Ca) of phosphate.

Glycosaminoglycans are a family of macromolecules containing long unbranched polysaccharides containing a repeating disaccharide unit. Preferably, the glycosaminoglycan is selected from one or more of chondroitin sulphate, dermatin sulphate, heparin, heparin sulphate, keratin sulphate and hyaluronic acid. Chondroitin sulphate may be chondroitin-4-sulphate or chondroitin-6-sulphate, both of which are commercially available, for example, from Sigma-Aldrich Inc. The chondroitin-6-sulphate may be derived from shark cartilage. Hyaluronic acid may be derived from human umbilical chord. Heparin may be derived from porcine intestinal mucosa.

The collagen may be soluble or insoluble and may be derived from any tissue in any animal and may be extracted using any number of conventional techniques.

Precipitation may be effected by combining the collagen, the calcium source, the phosphorous source and the glycosaminoglycan in an acidic aqueous solution and either allowing the solution to stand until precipitation occurs, agitating the solution, titration using basic titrants such as ammonia, addition of a nucleating agent such as pre-fabricated brushite, varying the rate of addition of the calcium source, or any combination of these or numerous other techniques known in the art.

The composite biomaterial according to the present invention is advantageously used as a tissue regeneration scaffold for musculoskeletal and dental applications.

The composite biomaterial according to the present invention may be used as a substitute bone or dental material. Accordingly, the present invention provides a synthetic bone material, bone implant, bone graft, bone substitute, bone scaffold, filler, coating or cement comprising a biomaterial as herein described.

The composite biomaterial is advantageously provided in the form of a multi-layered scaffold. In particular, the present invention provides tissue regeneration scaffolds for musculoskeletal and dental applications. Multilayer (i.e. two or more layers) scaffolds according to the present invention may find application in, for example, bone/cartilage interfaces (eg articular joints), bone/tendon interfaces (eg tendon insertion points), bone/ligament interfaces (eg ligament insertion points), and tooth/ligament interfaces (eg tooth/periodontal ligament juncture).

Although the present invention is primarily concerned with scaffolds for tissue engineering applications, the material according to the present invention may be used to fabricate implants that persist in the body for quite some time. For example, a semi-permanent implant may be necessary for tendon and ligament applications.

The present invention will now be described in relation to two preferred synthesis embodiments: solid-phase co-synthesis and solid-liquid co-synthesis. These techniques have been developed by the present inventors to allow fabrication of multi-component scaffolds with vastly dissimilar component properties. They provide a method for the production of continuous (soft) interfaces with a continuity of collagen fibrils between scaffold component layers that mimic those seen in vivo. They address the problems related to suturing or gluing dissimilar phases together after fabrication.

The solid-phase co-synthesis and solid-liquid co-synthesis methods according to the present invention offer the advantage that the individual scaffold components need not be formed at substantially the same time from the liquid state. This is in contrast to a liquid-phase co-synthesis where all slurries were layered and solidified together.

The synthesis methods comprise a sequence of steps that can be applied in any number of repetitions in order to produce a porous scaffold comprising a series of individual components. These individual components are fabricated separately from one another and are then joined together using any number of repetitions of the co-synthesis processes to form a single scaffold with regions of different structural, mechanical, or compositional characteristics (i.e., pore size, relative density, pore shape, stiffness, chemical composition, crosslinking density, degradation rate).

The solid-phase co-synthesis and solid-liquid co-synthesis methods will now be described further by way of example.

Solid-Phase Co-Synthesis

In the case of solid-phase co-synthesis, each component layer of the multi-component scaffold is fabricated separately. The final three-dimensional matrix of scaffold structures is then assembled from the separate component regions using a second freeze-drying procedure. A thin layer of, for example, collagen-based suspension is placed between each scaffold and allowed to absorb into the first few layers of pores in each scaffold. The scaffold is then freeze-dried a second time, resulting in an interpenetrating network of collagen fibers between each distinct scaffold component. This process may, of course, be repeated multiple times if desired.

Solid-Phase Co-Synthesis: Step 1: Slurry Preparation

Any combination of aqueous, collagen-based slurries can be fabricated. Detailed fabrication protocols exist for the production of type I collagen [10, 11], type II collagen [12], or mineralized type I collagen/GAG/brushite slurry (see, for example, PCT/GB04/004550).

Solid-Phase Co-Synthesis: Step 2: Fabrication of porous, collagen-based components Each component can be fabricated from distinct collagen-based slurries via freeze-drying. A variety of freeze-drying protocols have been published allowing the fabrication of scaffolds with different mean pore sizes, shapes, and orientations [10, 11, 13-15], and any of these protocols may be utilized to form each scaffold component. Briefly, each collagen-based suspension is placed into a mold; the mold can be in any desired shape and may be fabricated from any number of materials (i.e., polymers, metals, ceramics, glasses, or glass ceramics). The suspension is then solidified within the mold by exposing the mold to a refrigerated environment; solidification can take place rapidly or slowly, in a predominant direction or uniformly, and the temperature of the solidifying environment may be controlled in any manner to allow the suspension to fully solidify, resulting in an interpenetrating network of ice crystals surrounded by collagen fibers. The solidified suspension is then sublimated, removing the ice crystals and resulting in a porous component which on its own constitutes a homogeneous scaffold structure.

Any number of individual components may be fabricated from different suspensions, using different freezing protocols, and in different molds.

Solid-Phase Co-Synthesis: Step 3: Post-fabrication Processing

Any number of post-fabrication processing steps may be performed on each component following freeze-drying. Such post-fabrication processes include physical crosslinking techniques (i.e., dehydrothermal crosslinking, ultraviolet crosslinking) [11, 13, 16-18], chemical crosslinking techniques (i.e., carbodiimide-based crosslinking, gluteraldehyde-based crosslinking) [11, 16], or partial degradation of the scaffold using enzyme cocktails (i.e., collagenase, dispase). Following the use of any treatments that involve hydration of the scaffold, the liquid component can be removed using a second freeze-drying process. Again, any number of molding containers, freezing protocols, and sublimation protocols may be utilized to remove the liquid component from the scaffold.

Solid-Phase Co-Synthesis: Step 4: Solid Phase Co-Synthesis

Following complete processing of each component, the individual components may be joined together using solid phase co-synthesis. A thin layer of collagen-based suspension is placed between individual scaffold components. This process is repeated to join together all individual scaffold components into a larger scaffold with distinct regions. The collagen-based suspension locally hydrates the interface between each scaffold, temporarily sticking the scaffolds together. The assembled scaffold is then freeze-dried using one of any number of solidification and sublimation protocols; following freeze-drying, the scaffold components are held together by an interconnecting network of collagen fibers extending across each interface between scaffold components.

Solid-Phase Co-Synthesis: Step 5: Post-Fabrication Processing

After assembly of the larger scaffold structure, any number of post-fabrication processing steps can be utilized; such processes have already been listed in step 3. After such processing, the scaffold may be re-freeze-dried to produce a porous, collagen-based scaffold with any variety of dissimilar structural and compositional properties.

Solid-Liquid Co-Synthesis

In the case of solid-liquid co-synthesis, one or multiple component layers of the final scaffold are fabricated separately. The final three-dimensional matrix of scaffold structures is then assembled using an additional or multiple additional freeze-drying procedures. A collagen-based suspension, for example, is placed with already fabricated component or components and allowed to absorb into the component scaffolds. The suspension-scaffold system is then freeze-dried a second time, resulting in an interpenetrating network of collagen fibers between each distinct scaffold component. This process may, of course, be repeated multiple times if desired with additional suspensions/slurries so as to form the final scaffold structure.

The solid-liquid co-synthesis method is similar to the solid-phase co-synthesis method and comprises a sequence of steps that can be applied in any number of repetitions to produce a porous scaffold comprising a series of individual porous components. Also similar to the solid-phase co-synthesis method, one or more of the porous components, which on their own comprise homogeneous porous scaffolds, are conjoined via a freeze-drying technique. However, the solid-liquid co-synthesis method is distinguished from the solid-phase co-synthesis method by the fact that at least one of the components is formed, via freeze drying, from a slurry placed in integral contact with one or more previously fabricated components.

Solid-Liquid Co-Synthesis: Step 1: Slurry Preparation

Any combination of aqueous, collagen-based slurries can be fabricated. Detailed fabrication protocols exist for the production of type I collagen [10, 11], type II collagen [12], or mineralized type I collagen/GAG/brushite slurry (see, for example, PCT/GB04/004550).

Solid-Liquid Co-Synthesis: Step 2: Fabrication of Porous Components

The one or more component scaffolds are fabricated from the distinct collagen-based slurry(ies) using one or more of the freeze-drying techniques described above in relation to the solid-phase co-synthesis.

Solid-Liquid Co-Synthesis: Step 3: Post-Fabrication Processing of Previously Fabricated Porous Components Any number of post-fabrication processing steps may be performed on each scaffold component following freeze-drying described above in relation to the solid-phase co-synthesis.

Solid-Liquid Co-Synthesis: Step 4: Solid-Liquid Co-Synthesis

After complete processing of each scaffold component, one or more slurries are placed in integral contact with one or more of the previously fabricated porous components; the slurries are allowed to diffuse into the pores of their adjacent previously fabricated component or components for a designated period of time before said one or more slurries are solidified and then sublimated via freeze drying to form a multi-phase scaffold of new scaffold components integrally connected to the previously fabricated component or components. This step may be repeated any number of times to produce multi-phase scaffolds containing any number of components.

Solid-Liquid Co-Synthesis: Step 5: Post-Fabrication Processing

After assembly of the complete scaffold structure, any number of post-fabrication processing steps can be utilized; such processes have already been listed in step 3. After processing, the scaffold may be re-freeze-dried to produce a porous, collagen-based scaffold with any variety of dissimilar structural and compositional properties.

The processes according to present invention offer a number of advantages for the production of multi-component scaffolds. Notably:

Individually controlled physical (i.e., pore size, pore shape, crosslink density, degradation rate), mechanical (i.e., modulus), and chemical (i.e., mineral content, collagen content, glycosaminoglycan content) properties in distinct regions of the scaffold Improved cellular attachment via incorporation of collagen as a primary constituent Strong interfacial strength due to the interconnected collagen-fiber structure across boundaries between distinct components Limited chemical diffusion between adjacent layers of different chemical composition in the scaffold due to solid phase co-synthesis The present invention will now be described further with reference to the following Examples and Drawings, in which:

FIG. 1 shows a two-component scaffold fabricated by solid phase co-synthesis to form bilayer scaffold in accordance with Example 1C. The top region comprises an unmineralized, type II collagen scaffold, while the bottom region comprises a mineralized, type I collagen scaffold.

Figure 2:
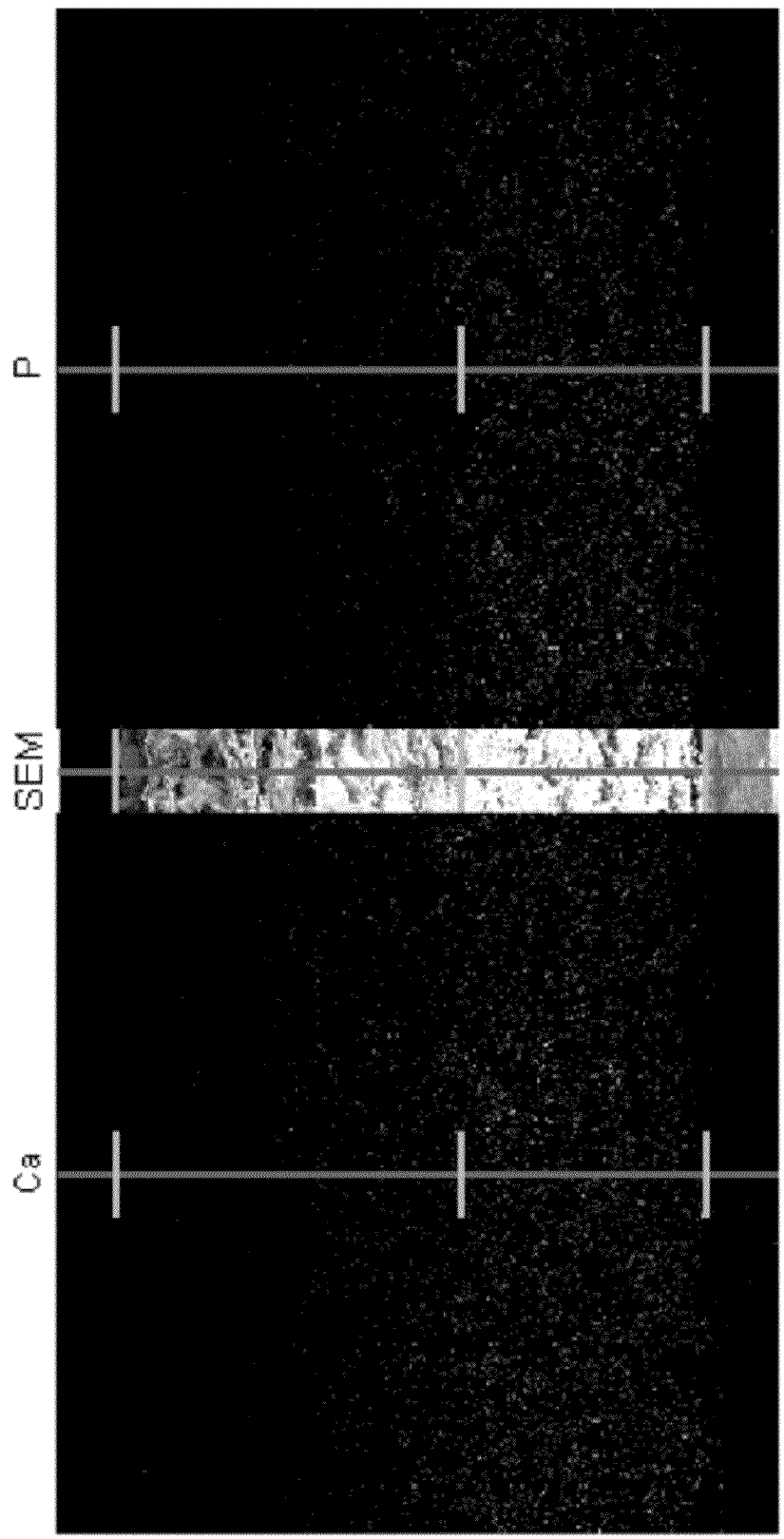
FIG. 2 shows elemental analysis of mineral (Ca and P) content in the layered scaffold fabricated by solid phase co-synthesis in accordance with Example 1C.

FIG. 2 shows elemental analysis of mineral (Ca and P) content in the layered scaffold fabricated by solid phase co-synthesis in accordance with Example 1C. The mineral content is found almost exclusively in the mineralized region (between the lower set of green lines).

Figure 3:
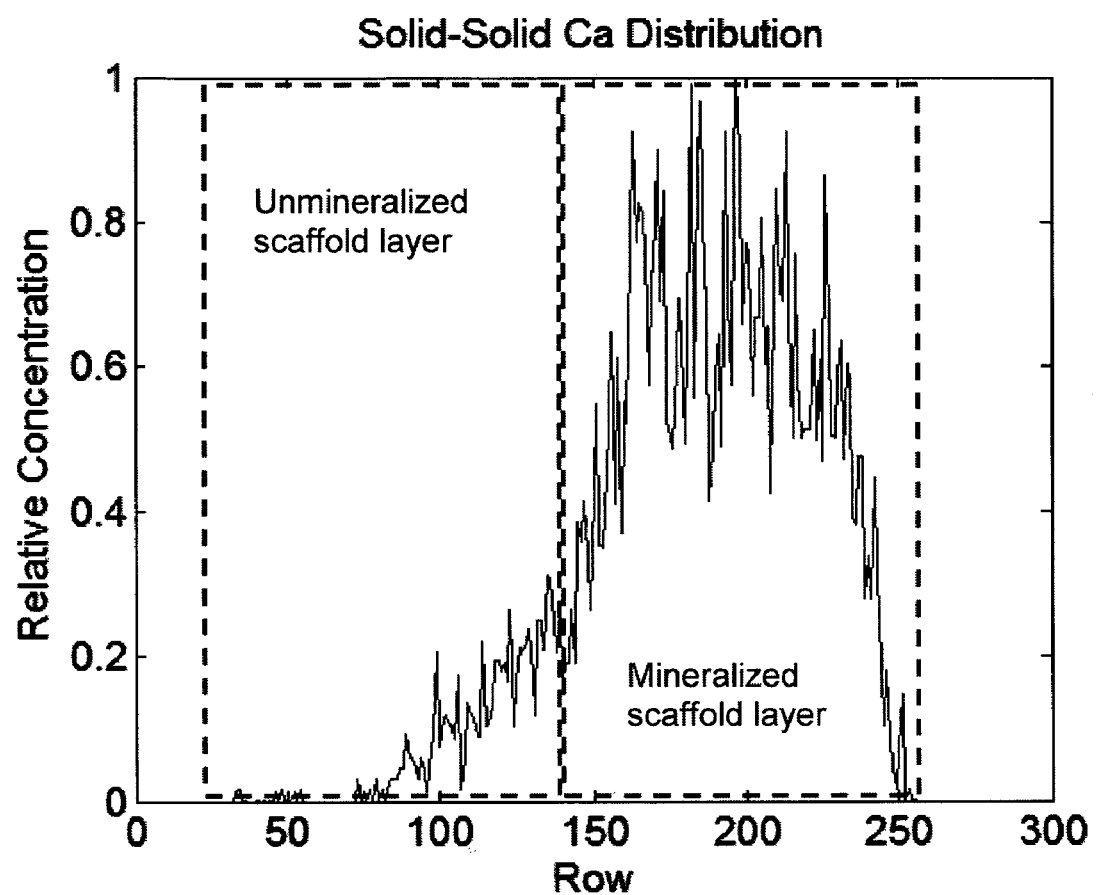
FIG. 3 shows the relative concentration of mineral in the layered scaffold formed from a mineralized type I collagen and an unmineralized type II collagen scaffold components in accordance with Example 1C.

FIG. 3 shows the relative concentration of mineral in the layered scaffold formed from a mineralized type I collagen and an unmineralized type II collagen scaffold components in accordance with Example 1C.

EXAMPLES

Example 1

Solid-Phase Co-Synthesis

A. Fabrication of Mineralized (Brushite) Type I Collagen-Glycosaminoglycan Scaffold Suspension Preparation:

A previously described in PCT/GB04/004550, a mineralized (brushite) collagen-glycosaminoglycan suspension was prepared from type I collagen (Integra LifeSciences Corp., Plainsboro, N.J., USA), chondroitin 6-sulfate (Sigma-Aldrich Inc, St. Louis, Mo., USA), orthophosphoric acid ($H_3PO_4$, BDH Laboratory Supply, Poole, UK), calcium hydroxide ($Ca(OH)_2$, Sigma-Aldrich Inc), and calcium nitrate ($Ca(NO_3)_2 \cdot 4H_2O$, Sigma-Aldrich Inc.).

Freeze-Drying:

A 10 mm layer of the mineralized (brushite) type I collagen-glycosaminoglycan suspension was placed into a rectangular (25 mm×50 mm) polysulfone mold with a bottom thickness of 8 mm. A previously described temperature ramping technique [10, 15] was utilized to solidify the mineralized (brushite) type I collagen-glycosaminoglycan suspension: the freeze-drier shelf temperature was ramped from room temperature to −20° C. at a pre-specified rate (3° C./min) and then held at −20° C. for a period of 600 minutes to allow for complete solidification [15]; after complete solidification, the frozen suspension was sublimated at a temperature of 25° C. for 24 hours at a pressure of 200 mTorr, resulting in the formation of a collagen-glycosaminoglycan scaffold with a mean pore size of greater than 250 μm.

Post Fabrication Processing:

The scaffold was removed from its mold and crosslinked using a pre-specified carbodiimide (liquid chemical based) crosslinking treatment [16]. After crosslinking, the scaffold was washed repeatedly in phosphate buffered saline (PBS, Sigma-Aldrich Inc.) and deionized water. The hydrated scaffold was placed back in the freeze-drier at a constant temperature of −40° C. for 60 minutes, followed by sublimation (0° C., 17 hours, 200 mTorr) to remove the liquid content from the scaffold.

B. Fabrication of Unmineralized Type II Collagen-Glycosaminoglycan Scaffold

Suspension Preparation:

A prefabricated type II collagen-glycosaminoglycan suspension (Geistlich Biomaterials, Wolhusen, Switzerland) [12], was removed form the refrigerator and allowed to return to room temperature.

Freeze-Drying:

A 3 mm layer of the type II collagen-glycosaminoglycan suspension was placed into a rectangular (25 mm×50 mm) polysulfone mold with a bottom thickness of 8 mm. A previously described temperature ramping technique [10, 15] was utilized to solidify the type II collagen-glycosaminoglycan suspension. The freeze-drier shelf temperature was ramped from room temperature to −40° C. at a pre-specified rate (1.4° C./min) and then held at −40° C. for a period of 60 minutes to allow for complete solidification [15]; after complete solidification, the frozen suspension was sublimated at a temperature of 0° C. for 17 hours at a pressure of 200 mTorr, resulting in the formation of a collagen-glycosaminoglycan scaffold with a mean pore size of approximately 100 μm.

Post Fabrication Processing:

The scaffold was removed from its polysulfone mold and crosslinked using a previously described dehydrothermal crosslinking treatment in order to increase scaffold stiffness and reduce scaffold degradation rate [11, 13]; briefly, dehydrothermal crosslinking was performed at a temperature of 105° C. for 24 hours at a pressure of 50 mTorr.

C. Solid Phase Co-Synthesis to Form Bilayer Scaffold

Suspension Preparation:

A small volume of a previously described unmineralized type I collagen-glycosaminoglycan suspension was prepared from type I collagen (Integra LifeSciences Inc.), acetic acid (Sigma-Aldrich Inc.), and chondroitin 6-sulfate (Sigma-Aldrich Inc.) [10, 11, 15].

Solid Phase Co-Synthesis:

The mineralized (brushite) type I collagen-glycosaminoglycan scaffold was placed into the rectangular polysulfone mold used during initial scaffold fabrication. A thin layer of the unmineralized type I collagen-glycosaminoglycan suspension was spread across the top surface of the mineralized (brushite) scaffold. The type II collagen-glycosaminoglycan scaffold was placed on top to the suspension layer. Both scaffolds were hydrated by the collagen-glycosaminoglycan suspension along the interface.

A previously described temperature ramping technique [10, 15] was utilized to solidify the type I collagen-glycosaminoglycan suspension along the interface between the two previously formed scaffolds. The freeze-drier shelf temperature was ramped from room temperature to −40° C. at a pre-specified rate (1.4° C./min) and then held at −40° C. for a period of 60 minutes to allow for complete solidification [15]; after complete solidification, the frozen suspension was sublimated at a temperature of 0° C. for 17 hours at a pressure of 200 mTorr.

This process results in the fabrication of a layered scaffold with two distinct regions (mineralized type I collagen-glycosaminoglycan and unmineralized type II collagen-glycosaminoglycan scaffold). The two scaffold layers are held together by a thin type I collagen-glycosaminoglycan scaffold structure extending across the interface between the two original scaffolds (see FIGS. 1-3).

Example 2

Solid-Liquid Co-Synthesis

A. Fabrication of Mineralized (Brushite) Type I Collagen-Glycosaminoglycan Scaffold Suspension Preparation:

A previously described (see PCT/GB04/004550) mineralized (brushite) collagen-glycosaminoglycan suspension was prepared from type I collagen (Integra LifeSciences Corp., Plainsboro, N.J., USA), chondroitin 6-sulfate (Sigma-Aldrich Inc, St. Louis, Mo., USA), orthophosphoric acid ($H_3PO_4$, BDH Laboratory Supply, Poole, UK), calcium hydroxide ($Ca(OH)_2$, Sigma-Aldrich Inc), and calcium nitrate ($Ca(NO_3)_2 \cdot 4H_2O$, Sigma-Aldrich Inc.).

Freeze-Drying:

A 10 mm layer of the mineralized (brushite) type I collagen-glycosaminoglycan suspension was placed into a rectangular (25 mm×50 mm) polysulfone mold with a bottom thickness of 8 mm. A previously described temperature ramping technique [10, 15] was utilized to solidify the mineralized (brushite) type I collagen-glycosaminoglycan suspension. The freeze-drier shelf temperature was ramped from room temperature to −20° C. at a pre-specified rate (3° C./min) and then held at −20° C. for a period of 600 minutes to allow for complete solidification [15]; after complete solidification, the frozen suspension was sublimated at a temperature of 25° C. for 24 hours at a pressure of 200 mTorr, resulting in the formation of a collagen-glycosaminoglycan scaffold with a mean pore size of greater than 250 μm.

Post Fabrication Processing:

The scaffold was removed from its mold and crosslinked using a pre-specified carbodiimide (liquid chemical based) crosslinking treatment [16]. After crosslinking, the scaffold was washed repeatedly in phosphate buffered saline (PBS, Sigma-Aldrich Inc.) and deionized water. The hydrated scaffold was placed back in the freeze-drier at a constant temperature of −40° C. for 60 minutes, followed by sublimation (0° C., 17 hours, 200 mTorr) to remove the liquid content from the scaffold.

B. Solid-Liquid Co-Synthesis to Form Bilayer Scaffold

Suspension Preparation:

A refrigerated, highly viscous slurry comprising a suspension of type I bovine Achilles tendon collagen in 0.05M phosphoric acid (Devro Casings, Moodiesburn, Chyston, Scotland) was allowed to return to room temperature.

Solid-Liquid Co-Synthesis:

The mineralized (brushite) type I collagen-glycosaminoglycan porous component was placed into the rectangular polysulfone mold used during initial scaffold fabrication. A 2 mm layer of the highly-viscous type I collagen suspension was then spread across the top surface of the mineralized porous component and allowed to infiltrate the near-surface regions of the pore structure by allowing the porous component/slurry construct to sit for 15 minutes.

A previously described temperature ramping technique [10, 15] was utilized to solidify the highly viscous type I collagen suspension. The freeze-drier shelf temperature was ramped from room temperature to −40° C. at a pre-specified rate (1.4° C./min) and then held at −40° C. for a period of 60 minutes to allow for complete solidification [15]; after solidification, the frozen suspension was sublimated at a temperature of 0° C. for 17 hours at a pressure of 200 mTorr.

Post Fabrication Processing:

The scaffold was removed from its polysulfone mold and crosslinked using a previously described carbodiimide crosslinking treatment [19] to increase scaffold stiffness and reduce scaffold degradation rate.

This process results in the fabrication of a layered scaffold with two distinct regions (mineralized type I collagen-glycosaminoglycan and unmineralized type I collagen layers).

The present invention describes novel processes for fabricating large, porous scaffolds with regions of dissimilar structural, compositional, and mechanical properties. The first process involves solid phase co-synthesis. The second process involves solid-liquid co-synthesis.

Solid phase co-synthesis allows dissimilar components of a larger scaffold structure to be fabricated separately and then attached together via thin layers of, for example, collagen-based slurries that are freeze-dried to form an interpenetrating collagen fiber network. This process allows fabrication of specialized scaffolds that have controlled physical (i.e., pore size, pore shape, crosslink density, degradation rate), mechanical (i.e., modulus), and chemical (i.e. mineral content, collagen content, glycosaminoglycan content) properties in distinct regions.

Solid-liquid co-synthesis allows dissimilar scaffold components to be fabricated separately and then assembled along with other slurries into a larger scaffold structure via freeze-drying. This process allows fabrication of specialized scaffolds that have controlled physical (i.e., pore size, pore shape, crosslink density, degradation rate), mechanical (i.e., modulus), and chemical (i.e., mineral content, collagen content, glycosaminoglycan content) properties in distinct regions. Especially important is the strong interfacial strength between distinct scaffold regions achieved using the solid phase co-synthesis and solid-liquid co-synthesis methods and the ability to control chemical diffusion between adjacent scaffold regions in cases where chemical diffusion between scaffold constituents is not beneficial.

REFERENCES

1. Yannas I V. Tissue and Organ Regeneration in Adults. New York: Springer; 2001.
2. Hunziker E B, Driesang I M K. Functional Barrier Principle for Growth-Factor-Based Articular Cartilage Repair. Osteoarthritis and Cartilage 2003; 11(5):320-327.
3. Gao J, Dennis J E, Solchaga L A, Awadallah A S, Goldberg V M, Caplan A I. Tissue-Engineered Fabrication of an Osteochondral Composite Graft Using Rat Bone Marrow-Derived Mesenchymal Stem Cells. Tissue Engineering 2001; 7(4):363-371.
4. Gao J, Dennis J E, Solchaga L A, Goldberg V M, Caplan A I. Repair of Osteochondral Defect with Tissue-Engineered Two-Phase Composite Material of Injectable Calcium Phosphate and Hyaluronan Sponge. Tissue Engineering 2002; 8(5):827-837.
5. Hung C T, Lima E G, Mauck R L, Taki E, LeRoux M A, Lu H H, et al. Anatomically Shaped Osteochondral Constructs for Articular Cartilage Repair. Journal of Biomechanics 2003; 36:1853-1864.
6. Niederauer G G, Slivka M A, Leatherbury N C, Korvick D L, H. H. H J, Ehler W C, et al. Evaluation of Multiphase Implants for Repair of Focal Osteochondral Defects in Goats. Biomaterials 2000; 21:2561-2574.
7. Schaefer D, Martin I, Shastri P, Padera R F, Langer R, Freed L E, et al. In Vitro Generation of Osteochondral Composites. Biomaterials 2000; 21(24):2599-2606.
8. Schaefer D, Martin I, Jundt G, Seidel J, Heberer M, Grodzinsky A, et al. Tissue-Engineered Composites for the Repair of Large Osteochondral Defects. Arthritis and Rheumatism 2002; 46(9):2524-2534.
9. Sherwood J K, Riley S L, Palazzolo R, Brown S C, Monkhouse D C, Coates M, et al. A Three-Dimensional Osteochondral Composite Scaffold for Articular Cartilage Repair. Biomaterials 2002; 23:4739-4751.
10. O'Brien F J, Harley B A, Yannas I V, Gibson L J. Influence of freezing rate on pore structure in freeze-dried collagen-GAG scaffolds. Biomaterials 2004; 25(6):1077-1086.
11. Yannas I V, Lee E, Orgill D P, Skrabut E M, Murphy G F. Synthesis and characterization of a model extracellular matrix that induces partial regeneration of adult mammalian skin. Proc. Natl. Acad. Sci. USA 1989; 86(3):933-937.
12. Gordon T D, Schloesser L, Humphries D E, Spector M. Effects of the degradation rate of collagen matrices on articular chondrocyte proliferation and biosynthesis in vitro. Tissue Eng. 2004; 10(7-8):1287-1295.
13. Harley B A, Spilker M H, Wu J W, Asano K, Hsu H-P, Spector M, et al. Optimal degradation rate for collagen chambers used for regeneration of peripheral nerves over long gaps. Cells Tissues Organs 2004; 176(1-3):153-165.
14. Loree H M, Yannas I V, Mikic B, Chang A S, Perutz S M, Norregaard T V, et al. A freeze-drying process for fabrication of polymeric bridges for peripheral nerve regeneration. In: Proc. 15th Annual Northeast Bioeng. Conf.; 1989; 1989. p. 53-54.
15. O'Brien F J, Harley B A, Yannas I V, Gibson L J. The effect of pore size on cell adhesion in collagen-GAG scaffolds. Biomaterials 2005; 26(4):433-441.
16. Lee C R, Grodzinsky A J, Spector M. The effects of crosslinking of collagen-glycosaminoglycan scaffolds on compressive stiffness, chondrocyte-mediated contraction, proliferation, and biosynthesis. Biomaterials 2001; 22:3145-3154.
17. Yannas I V, Burke J F, Huang C, Gordon P L. Correlation of in vivo collagen degradation rate with in vitro measurements. J Biomed Mater Res 1975; 9(6):623-628.
18. Yannas I V, Tobolsky A V. Cross linking of gelatine by dehydration. Nature 1967; 215(100):509-510.
19. Olde Damink L H H, Dijkstra P J, van Luyn M J A, Van Wachem P B, Nieuwenhuis P, Feijen J. Cross-linking of dermal sheep collagen using a water soluble carbodiimide. Biomaterials 1996; 17:765-773.

ANNEX

The content of the applicant's earlier International patent application, PCT/GB2006/000797, filed 6 Mar. 2006, is set out below.

The present invention relates to the field of synthetic bone materials for biomedical applications and, in particular, to porous monolithic and porous layered scaffolds comprising collagen, calcium phosphate, and optionally a glycosaminoglycan for use in tissue engineering.

Natural bone is a biocomposite of collagen, non-collagenous organic phases including glycosaminoglycans, and calcium phosphate. Its complex hierarchical structure leads to exceptional mechanical properties including high stiffness, strength, and fracture toughness, which in turn enable bones to withstand the physiological stresses to which they are subjected on a daily basis. The challenge faced by researchers in the field is to make a synthetic material that has a composition and structure that will allow natural bone growth in and around the synthetic material in the human or animal body.

It has been observed that bone will bond directly to calcium phosphates in the human body (a property referred to as bioactivity) through a bone-like apatite layer formed in the body environment. Collagen and copolymers comprising collagen and other bioorganics such as glycosaminoglycans on the other hand, are known to be optimal substrates for the attachment and proliferation of numerous cell types, including those responsible for the production and maintenance of bone in the human body.

Hydroxyapatite is the calcium phosphate most commonly used as a constituent in bone substitute materials. It is, however, a relatively insoluble material when compared to other forms of calcium phosphate materials such as brushite, tricalcium phosphate and octacalcium phosphate. The relatively low solubility of apatite can be a disadvantage when producing a biomaterial as the rate of resorption of the material in the body is particularly slow.

Calcium phosphates such as hydroxyapatite are mechanically stiff materials. However, they are relatively brittle when compared to natural bone. Collagen is a mechanically tough material, but has relatively low stiffness when compared to natural bone. Materials comprising copolymers of collagen and glycosaminoglycans are both tougher and stiffer than collagen alone, but still have relatively low stiffness when compared to natural bone.

Previous attempts to produce a synthetic bone-substitute material having improved mechanical toughness over hydroxyapatite and improved stiffness over collagen and copolymers of collagen and glycosaminoglycans include combining collagen and apatite by mechanical mixing. Such a mechanical method is described in EP-A-0164 484.

Later developments include producing a bone-replacement material comprising hydroxyapatite, collagen and chondroitin-4-sulphate by the mechanical mixing of these components. This is described in EP-A-0214070. This document further describes dehydrothermic crosslinking of the chondroitin-4-sulphate to the collagen. Materials comprising apatite, collagen and chondroitin-4-sulphate have been found to have good biocompatibility. The mechanical mixing of the apatite with the collagen, and optionally chondroitin-4-sulphate, essentially forms collagen/chondroitin-4-sulphate-coated particles of apatite. It has been found that such a material, although biocompatible, produces limited in-growth of natural bone when in the human or animal body and no remodeling of the calcium phosphate phase of the synthetic material.

The repair of skeletal sites compromised by trauma, deformity or disease poses a special challenge to orthopaedic surgeons in that, unlike defects in skin, nerve and most other tissue types, skeletal defects encompass multiple, distinct tissue types (i.e. bone, cartilage, tendon and ligament), involve locations that undergo regular mechanical loading, and traverse interfaces between mineralised to unmineralised tissues (e.g. ligament insertion points, the "tidemark" at the bone/cartilage interface).

Existing clinical approaches address the repair of skeletal defects either with non-resorbable prosthetic implants, autologous or allogenous tissue grafts, chemical agents, cell transplantation or combinations of these methods. While these approaches have achieved some success for the treatment of single tissue types, cases where interfaces between mineralised and unmineralised tissue are involved, such as articular joint defects for example, result in healing that is, at best, incomplete. Furthermore, even the most successful of the existing treatments require either the harvest of tissue from a donor site and/or the suturing to bone, cartilage, ligament or tendon. The former procedure suffers from lack of donor sites and donor site morbidity, while the latter is difficult to implement and creates additional defects in the form of suture holes.

The terms composite scaffold and layered scaffold are synonymous, and refer to scaffolds comprising two or more layers, with the material composition of each layer differing substantially from the material composition of its adjacent layer or layers. The term single-layered scaffold or monolithic scaffold are synonymous, and refer to scaffolds comprising one layer only, with the material composition within each layer being largely homogeneous throughout.

A limited number of recent efforts have sought to develop tissue-engineering strategies that employ porous, layered scaffolds for the treatment of articular joint defects involving either cartilage alone or both bone and cartilage. These constructs seek to induce the regeneration of bone and cartilage concurrently, but using separate scaffolds for each (Niederauer et al., 2000; Schaefer et al., 2000; Gao et al., 2001; Gao et al., 2002; Schaefer et al., 2002; Sherwood et al., 2002; Hung et al., 2003; Hunziker and Driesang, 2003).

An additional feature of layered scaffolds is the potential they hold for achieving sutureless fixation via direct attachment of the bony layer to the subchondral bone plate. Provided the cartilaginous portion remains firmly attached to the bony portion, no additional fixation is required. Sutureless fixation may also enable the treatment of defects involving insertions points of tendon and ligament to bone.

Despite the promise of this new approach, two shortcomings can limit the effectiveness of the layered scaffolds reported to date. The first relates to the materials used for the respective layers of the scaffold. Resorbable synthetic polymers have been the only material used for the cartilaginous layer, and have often been a component of the osseous portion in many of these scaffolds as well. Although easy to fabricate, synthetic polymers are known to be less conducive to cell attachment and proliferation than natural polymers such as collagen, and can furthermore release high concentrations of acid as they degrade. Moreover, for applications where tendon or ligament repair is necessary, resorbable synthetic polymers, regardless of the manner in which they are crosslinked, have inadequate strength and stiffness to withstand even the reduced load applied during rehabilitation exercises.

The second shortcoming of conventional layered scaffolds relates to the interface between the respective layers. Natural articular joints and tendon/ligament insertion points are characterised by continuity of collagen fibrils between the mineralised and unmineralised regions. The resultant system of smooth transitions (soft interfaces) imparts an intrinsic mechanical stability to these sites, allowing them to withstand physiological loading without mechanical failure. In contrast, the majority of existing layered scaffolds contain hard interfaces, forming a distinct boundary between two dissimilar materials. Suturing (Schaefer et al., 2000), fibrin adhesive bonding (Gao et al., 2001) and other techniques (Gao et al., 2002; Hung et al., 2003) have been used to strengthen this interface. However, interfacial debonding has still been reported even in controlled animal models. These suturing and bonding methods are also delicate and poorly reproducible.

Previous work has developed means through which the parameters of freeze-drying protocols can be controlled to produce porous scaffolds of collagen and one or more glycosaminoglycans (GAGs) (Yannas et al., 1989; O'Brien et al., 2004; O'Brien et al., 2005; Loree et al 1989).)

These techniques allow scaffold features such as pore size and aspect ratio to be varied in a controlled manner, parameters known to have marked effects on the healing response at sites of trauma or injury. However, for treatment of injuries involving skeletal and musculoskeletal defects, it is necessary to develop technologies to produce porous scaffolds with material compositions and mechanical characteristics that closely match those of bone, as opposed to those of unmineralised collagen-GAG scaffolds.

The present invention seeks to address at least some of the problems associated with the prior art.

A process for the preparation of a composite biomaterial comprising an inorganic material and an organic material, the process comprising:

(a) providing a first slurry composition comprising a liquid carrier, an inorganic material and an organic material;
(b) providing a mould for the slurry;
(c) depositing the slurry in the mould;
(d) cooling the slurry deposited in the mould to a temperature at which the liquid carrier transforms into a plurality of solid crystals or particles;
(e) removing at least some of the plurality of solid crystals or particles, preferably by sublimation and/or evaporation, to leave a porous composite material comprising an inorganic material and an organic material; and
(f) removing the material from the mould.

The term biomaterial as used herein means a material that is biocompatible with a human or animal body.

The term slurry as used herein encompasses slurries, solutions, suspensions, colloids and dispersions.

The inorganic material will typically comprise a calcium phosphate material.

The organic material will typically comprise a bio-orgainic species, for example one that can solubilised or suspended in an aqueous medium to form a slurry. Examples include one or more of albumin, glycosaminoglycans, hyaluronan, chitosan, and synthetic polypeptides comprising a portion of the polypeptide sequence of collagen. Collagen is the preferred material, optionally together with a glycosaminoglycan.

The term collagen as used herein encompasses recombinant human (rh) collagen.

In a preferred embodiment, the inorganic material comprises a calcium phosphate material, the organic material comprises collagen and optionally a glycosaminoglycan. This results in a porous composite material comprising the calcium phosphate material and collagen and optionally a glycosaminoglycan. Preferably, the first slurry comprises a co-precipitate of collagen and the calcium phosphate material. More preferably, the first slurry comprises a triple co-precipitate of collagen, a calcium phosphate material and a glycosaminoglycan.

Alternatively, the first slurry may simply comprise a mechanical mixture of collagen and the calcium phosphate material and optionally the glycosaminoglycan. This may be produced by a conventional technique such as described in, for example, EP-A-0164 484 and EP-A-0214070. While a mechanical mixture may be used to form the slurry, a co-precipitate of collagen and the calcium phosphate material or a triple co-precipitate of collagen, the calcium phosphate material and a glycosaminoglycan are preferred.

The calcium phosphate material may be selected, for example, from one or more of brushite, octacalcium phosphate and/or apatite. The calcium phosphate material preferably comprises brushite.

The pH of the slurry is preferably from 2.5 to 6.5, more preferably from 2.5 to 5.5, still more preferably from 3.0 to 4.5, and still more preferably from 3.8 to 4.2.

The slurry composition may comprise one or more glycosaminoglycans. The slurry composition may comprise one or more calcium phosphate materials.

The presence of other species (e.g. silver, silicon, silica, table salt, sugar, etc) in the precursor slurry is not precluded.

At least some of the plurality of solid crystals or particles may be removed by sublimation and/or evaporation to leave a porous composite material comprising collagen, a calcium phosphate material, and optionally a glycosaminoglycan. The preferred method is sublimation.

Steps (d) and (e) may be effected by a freeze-drying technique. If the liquid carrier is water, the sublimation step comprises reducing the pressure in the environment around the mould and frozen slurry to below the triple point of the water/ice/water vapour system, followed by elevation of the temperature to greater than the temperature of the solid-vapor transition temperature at the achieved vacuum pressure. The ice in the product is directly converted into vapor via sublimation as long as the ambient partial liquid vapor pressure is lower than the partial pressure of the frozen liquid at its current temperature. The temperature is typically elevated to at or above 0° C. This step is performed to remove the ice crystals from the frozen slurry via sublimation.

The freeze-drying parameters may be adjusted to control pore size and aspect ratio as desired. In general, slower cooling rates and higher final freezing temperatures (for example, cooling at approximately 0.25° C. per minute to a temperature of about −10° C.) favour large pores with higher aspect ratios, while faster cooling rates and lower final freezing temperatures (for example, cooling at approximately 2.5° C. per minute to a temperature of about −40° C.) favours the formation of small equiaxed pores.

The term "mould" as used herein is intended to encompass any mould, container or substrate capable of shaping, holding or supporting the slurry composition. Thus, the mould in its simplest form could simply comprise a supporting surface. The mould may be any desired shape, and may be fabricated from any suitable material including polymers (such as polysulphone, polypropylene, polyethylene), metals (such as stainless steel, titanium, cobalt chrome), ceramics (such as alumina, zirconia), glass ceramics, and glasses (such as borosilicate glass).

The applicant's earlier application, PCT/GB04/004550, filed 28 Oct. 2004, describes a triple co-precipitate of collagen, brushite and a glycosaminoglycan and a process for its preparation. The content of PCT/GB04/004550 is incorporated herein by reference.

The process described in PCT/GB04/004550 involves: providing an acidic aqueous solution comprising collagen, a calcium source and a phosphorous source and a glycosaminoglycan; and precipitating the collagen, the brushite and the glycosaminoglycan together from the aqueous solution to form a triple co-precipitate.

The term co-precipitate means precipitation of the two or three compounds where the compounds have been precipitated at substantially the same time from the same solution/dispersion. It is to be distinguished from a material formed from the mechanical mixing of the components, particularly where these components have been precipitated separately, for instance in different solutions. The microstructure of a co-precipitate is substantially different from a material formed from the mechanical mixing of its components.

In the process for preparing the co-precipitate, the calcium source is preferably selected from one or more of calcium nitrate, calcium acetate, calcium chloride, calcium carbonate, calcium alkoxide, calcium hydroxide, calcium silicate, calcium sulphate, calcium gluconate and the calcium salt of heparin. A calcium salt of heparin may be derived from the porcine intestinal mucosa. Suitable calcium salts are commercially available, for example, from Sigma-Aldrich Inc. The phosphorus source is preferably selected from one or more of ammonium-dihydrogen phosphate, diammonium hydrogen phosphate, phosphoric acid, disodium hydrogen orthophosphate 2-hydrate ($Na_2HPO_4.2H_2O$, sometimes termed GPR Sorensen's salt) and trimethyl phosphate, alkali metal salts (eg Na or K) of phosphate, alkaline earth salts (eg Mg or Ca) of phosphate.

Glycosaminoglycans are a family of macromolecules containing long unbranched polysaccharides containing a repeating disaccharide unit. Preferably, the glycosaminoglycan is selected from one or more of chondroitin sulphate, dermatin sulphate, heparin, heparin sulphate, keratin sulphate and hyaluronic acid. Chondroitin sulphate may be chondroitin-4-sulphate or chondroitin-6-sulphate, both of which are commercially available, for example, from Sigma-Aldrich Inc. The chondroitin-6-sulphate may be derived from shark cartilage. Hyaluronic acid may be derived from human umbilical chord. Heparin may be derived from porcine intestinal mucosa.

The collagen may be soluble or insoluble and may be derived from any tissue in any animal and may be extracted using any number of conventional techniques.

Precipitation may be effected by combining the collagen, the calcium source, the phosphorous source and the glycosaminoglycan in an acidic aqueous solution and either allowing the solution to stand until precipitation occurs, agitating the solution, titration using basic titrants such as ammonia, addition of a nucleating agent such as pre-fabricated brushite, varying the rate of addition of the calcium source, or any combination of these or numerous other techniques known in the art.

It will be appreciated that other components may be present in the slurry. For example, growth factors, genes, drugs or other biologically active species may optionally be added, alone or in combination, to the slurry.

In a preferred embodiment, the process according to the present invention advantageously further comprises:

providing a second slurry composition comprising a liquid carrier and an organic material and optionally an inorganic material; and prior to said cooling step, depositing said second slurry composition in the mould either before or after said first slurry composition has been deposited.

As before, the organic material will typically comprise one or more of collagen (including recombinant human (rh) collagen), a glycosaminoglycan, albumin, hyaluronan, chitosan, and synthetic polypeptides comprising a portion of the polypeptide sequence of collagen.

The second slurry composition may comprise an inorganic material such as, for example, a calcium phosphate material.

Preferably, the second slurry composition comprises a liquid carrier, collagen, optionally a calcium phosphate material, and optionally a glycosaminoglycan. In this embodiment, the second slurry composition preferably comprises a co-precipitate of collagen and a glycosaminoglycan, or a co-precipitate of collagen and a calcium phosphate material, or a triple co-precipitate of collagen, a glycosaminoglycan and a calcium phosphate material. Co-precipitation has already been discussed in relation to the preparation of the first slurry.

Alternatively, the second slurry may simply comprise a mechanical mixture of collagen and optionally one or both of a calcium phosphate material and a glycosaminoglycan. Mechanical mixtures have already been discussed in relation to the preparation of the first slurry.

If present, the calcium phosphate material in the second slurry may be selected from one or more of brushite, octacalcium phosphate and/or apatite.

The first and second slurry compositions will typically be deposited as first and second layers in the mould. For example, the first slurry is deposited in the mould, followed by the second slurry. The mould contents may then be subjected to steps (d), (e) and (f). Accordingly, the process may be used to form a multi-layered material, at least one layer of which preferably comprises a porous composite material comprising collagen, a calcium phosphate material, and optionally a glycosaminoglycan. The layer resulting from the second slurry composition may be a porous or a non-porous layer. If a porous layer is desired, then the pores can be created by sublimation and/or evaporation of a plurality of solid crystals or particles formed in the second slurry. This technique has been already discussed in relation to the first slurry and preferably comprises a freeze drying technique.

The process is carried out in the liquid phase and this is conducive to diffusion between the first slurry layer and the second slurry layer.

The layers may be deposited in any manner of layering orders or geometries. The layers may, for example, be situated vertically (i.e. one on top of the other), horizontally (i.e. one beside the other), and/or radially (one spherical layer on top of the next).

The casting process according to the present invention enables the fabrication of porous monolithic and porous layered scaffolds for use in tissue engineering.

After the first and second slurry compositions have been deposited in the mould, the contents of the mould are preferably left to rest for up to 24 hours before the cooling step.

This is advantageous because it allows inter-diffusion of the various slurry constituents between adjacent layers. This results in an improvement in inter-layer bond strength.

The liquid carrier in the first slurry preferably comprises water. The liquid carrier in the second slurry also preferably comprises water.

It will be appreciated that further slurry layers may be deposited in the mould prior to said cooling step, either before or after said first and/or second slurry composition(s) has/have been deposited.

The temperature of the slurry deposited in the mould prior to the cooling step will generally have an effect on the viscosity of the slurry. If the temperature is too high, then this may result in slurries of excessively low viscosity, which may result in complete (and therefore undesirable) intermixing of the first and second layers once the second slurry is deposited. It should also be noted that too high a temperature may result in denaturation of the collagen. On the other hand, too low a temperature may result in slurries with viscosities too high to allow efficient spreading, smoothing or shaping, and may risk the premature formation of ice crystals. Accordingly, the inventors have found that the temperature of the first slurry deposited in the mould prior to the cooling step is preferably in the range of from 2 to 40° C., more preferably from 4 to 37° C., still more preferably from 20 to 37° C. If multiple layered slurry compositions are used, then these ranges are also applicable to the additional slurries.

The step of cooling the first slurry deposited in the mould is preferably carried out to a temperature of $\leq 0°$ C. More preferably, the step of cooling is carried out to a temperature in the range of from −100 to 0° C., preferably from −80 to −10° C., more preferably from −40 to −20° C. If multiple layered slurry compositions are used, then these ranges are also applicable to the additional slurries.

The step of cooling the first slurry deposited in the mould is preferably carried out at a cooling rate of 0.02-10° C./min, more preferably from 0.02-6.0° C./min, still more preferably from 0.2-2.7° C./min. If multiple layered slurry compositions are used, then these ranges are also applicable to the additional slurries.

In general, slower cooling rates and higher final freezing temperatures (for example, cooling at 0.25° C. per minute to a temperature of −10° C.) favour large pores with higher aspect ratios, while faster cooling rates and lower final freezing temperatures (for example, cooling at 2.5° C. per minute to a temperature of −40° C.) favours the formation of small equiaxed pores.

The step of cooling the slurry deposited in the mould is preferably carried out at a pressure of from 1-200 kPa, more preferably from 50-150 kPa, still more preferably from 50-101.3 kPa. If multiple layered slurry compositions are used, then these ranges are also applicable to the additional slurries. The inventors have found that pressures below 50 kPa can result in the formation of bubbles within the slurry, while pressures greater than 200 kPa may induce excessive mixing of adjacent layers.

The thickness of the first slurry deposited in the mould is preferably from 0.1-500 mm, more preferably from 0.5-20 mm, still more preferably from 1.0-10 mm. If multiple layered slurry compositions are used, then these ranges are also applicable to the additional slurries. Layers in excess of 500 mm in thickness can be difficult to solidify completely, while layers less than 0.1 mm thick can freeze almost instantaneously, making it difficult to control accurately the progression of ice crystal nucleation and growth.

The viscosity of the first slurry prior to it being deposited in the mould is preferably from 0.1-50 Pa·s, more preferably from 0.1-10 Pa·s, still more preferably from 0.5-5 Pa·s. If multiple layered slurry compositions are used, then these ranges are also applicable to the additional slurries. Slurries with overly high viscosity can be difficult to spread, smooth and shape, while those with excessively low viscosity may result in complete (and therefore undesirable) intermixing of the first and second layers once the second slurry is deposited.

The step of removing at least some of the solid crystals or particles in the first slurry by sublimation is preferably carried out at a pressure of from 0-0.08 kPa, more preferably from 0.0025-0.08 kPa, still more preferably from 0.0025-0.04 kPa. If multiple layered slurry compositions are used, then these ranges are also applicable to the additional slurries. Pressures above that of the triple point of water (approximately 0.08 kPa) can risk the occurrence of melting instead of sublimation, while excessively low pressures are difficult to achieve, and unnecessary for encouraging sublimation.

With regard to the step of removing at least some of the solid crystals or particles in the first slurry by sublimation, if the duration of sublimation is too short, residual water and solvents can cause redissolution of the scaffold walls, thereby compromising the pore architecture. Accordingly, the inventors have found that this step is preferably carried out for up to 96 hours, more preferably from 12-72 hours, still more preferably from 24-36 hours. If multiple layered slurry compositions are used, then these ranges are also applicable to the additional slurries.

The step of removing at least some of the solid crystals or particles in the first slurry by sublimation is preferably carried out at a temperature of from −10-60° C., more preferably from 0-40° C., still more preferably from 20-37° C., still more preferably from 25-37° C. If multiple layered slurry compositions are used, then these ranges are also applicable to the additional slurries. If the temperature during sublimation is too low, the time required until sublimation is complete can become excessively long, while excessively high temperatures (i.e. above 40° C.) can risk denaturation of the collagen.

If the material comprises collagen and a glycosaminoglycan, then the process according to the present invention may further comprise the step of cross-linking the collagen and the glycosaminoglycan in the porous composite biomaterial. Cross-linking will typically take place after the material has been removed from the mould following sublimation. Crosslinking may be effected by subjecting the co-precipitate to one or more of gamma radiation, ultraviolet radiation, a dehyrdothermal treatment, non-enzymatic glycation with a simple sugar such as glucose, mannose, ribose and sucrose, contacting the triple co-precipitate with one or more of glutaraldehyde, carbodiimide (eg ethyl dimethylaminopropyl carbodiimide) and/or nor-dihydroguariaretic acid, or any combination of these methods. These methods are conventional in the art.

If the material comprises calcium phosphate, then the process according to the present invention may further comprise the step of converting at least some of the calcium phosphate material in the porous composite biomaterial to another calcium phosphate phase. For example, the process may comprise the step of converting at least some of the brushite in the porous composite biomaterial to octacalcium phosphate and/or apatite. The conversion of the brushite to octacalcium phosphate and/or apatite is preferably effected by hydrolysation. Phase conversion will typically take place after the material has been removed from the mould (and optionally cross-linked).

Apatite is a class of minerals comprising calcium and phosphate and has the general formula: $Ca_5(PO_4)_3(X)$, wherein X may be an ion that is typically $OH^-$, $F^-$ and $Cl^-$, as well as other ions known to those skilled in the art. The term apatite also includes substituted apatites such as silicon-substituted apatites. The term apatite includes hydroxyapatite, which is a specific example of an apatite. The hydroxyapatite may also be substituted with other species such as, for example, silicon.

As mentioned above, further slurry layers may be deposited in the mould prior to said cooling step, either before or after said first and/or second slurry composition(s) has/have been deposited. The further slurry layers will also typically comprise, for example, a liquid carrier, collagen, optionally a calcium phosphate material, and optionally a glycosaminoglycan. The contents of the mould are preferably left to rest for up to 24 hours before the cooling step so as to allow inter-diffusion of the various slurry constituents between adjacent layers.

Accordingly, the present invention provides a process for the preparation of a composite biomaterial comprising one, two, or more layers. At least one of the layers preferably comprises a porous biocomposite of collagen, a calcium phosphate material, and also preferably a glycosaminoglycan. All of the layers preferably contain collagen.

The composite biomaterial according to the present invention may be used to fabricate, for example, a porous monolithic scaffold, or a multi-layered scaffold in which at least one layer is porous. The composite biomaterial according to the present invention is advantageously used as a tissue regeneration scaffold for musculoskeletal and dental applications.

The process according to the present invention preferably involves incorporating collagen as an organic constituent in the first and second layers (collagen is preferably the major organic constituent in the first and second layers). If additional layers are present, then the process preferably involves incorporating collagen as an organic constituent in one or more of these further layers (collagen is also preferably the major organic constituent in the one or more further layers). The process involves fabricating all layers, and thus the interfaces between them, simultaneously in the liquid phase. This results in the creation of a strong interface between the layers through inter-diffusion. The term inter-diffusion refers to mixing that occurs as a result of molecular diffusion or Brownian motion when two slurries of differing composition are placed in integral contact.

In a second aspect, the present invention provides a synthetic composite biomaterial, wherein at least part of the biomaterial is formed from a porous co-precipitate comprising a calcium phosphate material and one or more of collagen (including recombinant human (rh) collagen), a glycosaminoglycan, albumin, hyaluronan, chitosan or a synthetic polypeptides comprising a portion of the polypeptide sequence of collagen, wherein the macropore size range (pore diameter) is preferably from 1-1000 microns, more preferably from 200-600 microns. The material preferably comprises collagen. The calcium phosphate material is preferably selected from one or more of brushite, octacalcium phosphate and/or apatite. The porous material preferably comprises a co-precipitate of the collagen and the calcium phosphate material. This has already been described in relation to the first aspect of the invention.

The term porous as used herein means that the material may contain macropores and/or micropores. Macroporosity typically refers to features associated with pores on the scale of greater than approximately 10 microns. Microporosity typically refers to features associated with pores on the scale of less than approximately 10 microns. It will be appreciated that there can be any combination of open and closed cells within the material. For example, the material will generally contain both macropores and micropores. The macroporosity is generally open-celled, although there may be a closed cell component.

The macropore size range (pore diameter) in the porous material according to the second aspect of the present invention is typically from 1 to 1200 microns, preferably from 10 to 1000 microns, more preferably from 100 to 800 microns, still more preferably from 200 to 600 microns.

The mean aspect ratio range in the porous material according to the second aspect of the present invention is preferably from 1 to 50, more preferably from 1 to 10, and most preferably approximately 1.

The pore size distribution (the standard deviation of the mean pore diameter) in the porous material according to the second aspect of the present invention is preferably from 1 to 800 microns, more preferably from 10 to 400 microns, and still more preferably from 20 to 200 microns.

The porosity in the porous material according to the second aspect of the present invention is preferably from 50 to 99.99 vol %, and more preferably from 70 to 98 vol %.

The percentage of open-cell porosity (measured as a percentage of the total number of pores both open- and closed-cell) in the porous material according to the second aspect of the present invention is preferably from 1 to 100%, more preferably from 20 to 100%, and still more preferably from 90 to 100%.

In a third aspect, the present invention provides a synthetic composite biomaterial, wherein at least part of the biomaterial is formed from a porous material comprising a calcium phosphate material and two or more of collagen (including recombinant human (rh) collagen), a glycosaminoglycan, albumin, hyaluronan, chitosan and a synthetic polypeptides comprising a portion of the polypeptide sequence of collagen. The material preferably comprises collagen and a glycosaminoglycan. The calcium phosphate material is preferably selected from one or more of brushite, octacalcium phosphate and/or apatite. The porous material preferably comprises a triple co-precipitate of collagen, a glycosaminoglycan and the calcium phosphate material. This has already been described in relation to the first aspect of the invention. The macropore size range (pore diameter) in the porous material according to the second aspect of the present invention is also applicable to the third aspect. The same is true for the mean aspect ratio range, the pore size distribution, the porosity and the percentage of open-cell porosity.

In a fourth aspect, the present invention provides a synthetic composite biomaterial comprising:

a first layer formed of a composite biomaterial according to the second or third aspect of the present invention; and a second layer joined to the first layer and formed of a material comprising collagen, or a co-precipitate of collagen and a glycosaminoglycan, or a co-precipitate of collagen and a calcium phosphate material, or a triple co-precipitate of collagen, a glycosaminoglycan and a calcium phosphate material. The calcium phosphate material is preferably selected from one or more of brushite, octacalcium phosphate and/or apatite.

The first and second layers are preferably integrally formed. Advantageously, this may be achieved by a process involving liquid phase co-synthesis. This encompasses any process in which adjacent layers, either dense or porous, of a material comprising multiple layers are formed by placing the slurries comprising the precursors to each layer in integral contact with each other before removal of the liquid carrier or carriers from said slurries, and in which removal of said liquid carrier or carriers from all layers is preferably performed at substantially the same time. Placing the precursor slurries in integral contact before removal of the liquid carrier (i.e. while still in the liquid phase) allows interdiffusion to occur between adjacent slurries. This results in a zone of interdiffusion at the interface between adjacent layers of the resulting material, within which the material composition is intermediate to the material compositions of the adjacent layers. The existence of a zone of interdiffusion can impart mechanical strength and stability to the interface between adjacent layers.

Accordingly, the first and second layers are preferably joined to one another through an inter-diffusion layer.

Alternatively, the first and second layers may be joined to one another through an inter-layer. The term inter-layer refers to any layer deposited independently between two other layers for the purpose of improving inter-layer bond strength or blocking the passage of cells, molecules or fluids between adjacent layers of the resulting scaffold, and may, for example, contain collagen, glycosaminoglycans, fibrin, anti-angiogenic drugs (e.g. suramin), growth factors, genes or any other constituents. An inter-layer is distinguished from an inter-diffusion layer by the fact that an inter-layer is deposited separately as a slurry whose composition is distinct from the composition of its adjacent layers, while an inter-diffusion layer is formed exclusively as a result of inter-diffusion between adjacent layers.

The first layer is porous. The second layer is also preferably porous, although it can be non-porous or substantially non-porous layer if desired.

The macropore size range (pore diameter) in the porous material according to the second aspect of the present invention is also applicable to the first and/or second layers in the embodiment according to the fourth aspect. The same is true for the mean aspect ratio range, the pore size distribution, the porosity and the percentage of open-cell porosity.

In any of the second, third and fourth aspects, the biomaterial may comprise one or more further layers joined to the first and/or second layers, each of said further layers preferably being formed of a material comprising collagen, or a co-precipitate of collagen and a glycosaminoglycan, or a co-precipitate of collagen and a calcium phosphate material, or a triple co-precipitate of collagen, a glycosaminoglycan, and a calcium phosphate material. The calcium phosphate material is preferably selected from one or more of brushite, octacalcium phosphate and/or apatite. The first and second layers and said one or more further layers are preferably integrally formed, and adjacent layers are preferably joined to one another through an inter-diffusion layer, which is typically formed by liquid phase co-synthesis. Generally, at least one of said further layers will be porous. Again, the macropore size range (pore diameter) in the porous material according to the second aspect of the present invention is also applicable to one or more of these further layers. The same is true for the mean aspect ratio range, the pore size distribution, the porosity and the percentage of open-cell porosity.

Differences in pore sizes between adjacent layers may vary from almost negligible to as great as +/−1000 microns.

Unless otherwise stated, the following description is applicable to any aspect of the present invention.

If the material comprises collagen and a glycosaminoglycan, then the collagen and the glycosaminoglycan may be crosslinked.

The collagen is preferably present in the material in an amount of from 1 to 99 wt %, preferably from 5 to 90 wt %, more preferably from 15 to 60 wt %.

The glycosaminoglycan is preferably present in the material in an amount of from 0.01 to 20 wt %, more preferably from 1 to 12 wt %, still more preferably from 1 to 5.5 wt %.

If the material comprises brushite, then the ratio of collagen to brushite is preferably from 10:1 to 1:100 by weight, more preferably from 5:1 to 1:20 by weight.

If the material comprises octacalcium phosphate, then the ratio of collagen to octacalcium phosphate is preferably 10:1 to 1:100 by weight, more preferably from 5:1 to 1:20 by weight.

The ratio of collagen to the glycosaminoglycan is preferably from 8:1 to 30:1 by weight.

The biomaterial according to the present invention may be used as a substitute bone or dental material. Accordingly, the present invention provides a synthetic bone material, bone implant, bone graft, bone substitute, bone scaffold, filler, coating or cement comprising a biomaterial as herein described.

The biomaterial is advantageously provided in the form of a multi-layered scaffold. In particular, the present invention provides tissue regeneration scaffolds for musculoskeletal and dental applications. Multilayer (i.e. two or more layers) scaffolds according to the present invention may find application in, for example, bone/cartilage interfaces (eg articular joints), bone/tendon interfaces (eg tendon insertion points), bone/ligament interfaces (eg ligament insertion points), and tooth/ligament interfaces (eg tooth/periodontal ligament juncture).

Although the present invention is primarily concerned with scaffolds for tissue engineering applications, the material according to the present invention may be used to fabricate implants that persist in the body for quite some time. For example, a semi-permanent implant may be necessary for tendon and ligament applications.

The present invention further provides a porous composite biomaterial obtainable by a process as herein described.

Synthesis Method

The present invention will now be described further by way of example. The preferred method of synthesis comprises a sequence of steps, which can be applied in whole or in part, to produce porous scaffolds having one or more layers at least one of which preferably comprises a triple co-precipitate of collagen, a glycosaminoglycan and a calcium phosphate material.

Step 0: Slurry Preparation

The preparation of mineralised collagen/GAG/brushite slurry or slurries may be achieved using the method outlined in the applicant's earlier patent application, PCT/GB04/004550, filed 28 Oct. 2004. The content of PCT/GB04/004550 is incorporated herein by reference.

The preparation of unmineralised collagen/GAG slurry or slurries may be achieved using a method as outlined in Yannas et al., 1989; O'Brien et al., 2004; O'Brien et al., 2005); Loree et al., (1989).

Growth factors, genes, drugs or other biologically active species may optionally be added, alone or in combination, to the slurry via mechanical mixing at this stage to facilitate their incorporation into the scaffold. In the case of scaffolds with more than one layer, the biologically active species incorporated into one layer need not be the same as the species incorporated into the next.

Step I: Casting
Step I-a: Casting of 1st layer
Step I-b: Casting of 2nd layer
Step I-c: Casting of 3rd layer
Step I-n: Casting of nth layer The casting step(s) involve the successive deposition of a slurry or slurries, in solution, suspension, colloid, or dispersion form, where water comprises the major diluent, into a mould, in which at least one of the slurries comprises a triple co-precipitate of collagen, one or more glycosaminoglycans and the calcium phosphate brushite, and all slurries contain collagen.

The mould may be any desired shape, and may be fabricated of any of a number of materials including polymers (such as polysulphone, polypropylene, polyethylene), metals (such as stainless steel, titanium, cobalt chrome) or ceramics (such as alumina, zirconia), glass ceramics, or glasses (such as borosilicate glass).

The mould may be constructed specifically to facilitate layering. Examples of suitable designs are shown in FIGS. 1 and 2.

The layers may, for example, be situated vertically (i.e. one on top of the other), horizontally (i.e. one beside the other), and/or radially (one spherical layer on top of the next).

In the event that the scaffold comprises one layer, the single layer to be cast comprises a slurry of a co-precipitate comprising collagen, a calcium phosphate material, which is preferably brushite, and optionally a glycosaminoglycan. Preferably, the slurry comprises a triple co-precipitate comprising collagen, brushite and a glycosaminoglycan. The preferred thickness of the layer is specified in the appropriate section of Table 1.

In the event that the scaffold comprises two layers, at least one of the layers to be cast comprises a slurry of a co-precipitate comprising collagen, a calcium phosphate material, which is preferably brushite, and optionally a glycosaminoglycan. Preferably, the slurry comprises a triple co-precipitate comprising collagen, brushite, and a glycosaminoglycan. The preferred thickness of this layer is specified in the appropriate section of Table 1. The other layer comprises a slurry comprising collagen, optionally a calcium phosphate material, and optionally a glycosaminoglycan. This slurry composition preferably comprises a co-precipitate of collagen and a glycosaminoglycan, a co-precipitate of collagen and a calcium phosphate material such as brushite, or a triple co-precipitate of collagen, a glycosaminoglycan and a calcium phosphate material, which is preferably brushite.

Further layers may be included as desired and these further layers are preferably formed from a slurry comprising collagen, optionally a calcium phosphate material, and optionally a glycosaminoglycan. The further slurry compositions preferably comprise a co-precipitate of collagen and a glycosaminoglycan, a co-precipitate of collagen and a calcium phosphate material such as brushite, or a triple co-precipitate of collagen, a glycosaminoglycan and a calcium phosphate material, which is preferably brushite.

The composition of the slurries in each subsequent layer may be identical, vary slightly, or vary significantly, provided that collagen and preferably also a glycosaminoglycan are present in each layer, and that at least one of the layers also contains a calcium phosphate material such as, for example, brushite.

Step II: Inter-Diffusion

The co-diffusion step involves allowing the respective layers of the cast, layered slurry to inter-diffuse. This step is performed for the purpose of allowing inter-diffusion of slurry constituents between adjacent layers, thereby increasing the inter-layer bond strength after solidification and sublimation. Preferred conditions for the inter-diffusion step are listed in the appropriate section of Table 2.

Step III: Controlled Cooling

The controlled cooling step involves placing the mould containing the slurry in an environment, which is then cooled at a controlled rate to a final temperature less than 0° C. This step is performed to initiate and control the rate of ice crystal nucleation and growth within the slurry. Ice crystals are then subsequently removed by sublimation leaving a porous scaffold. The architecture of the ice crystal network will determine the ultimate pore structure of the scaffold. The preferred parameters for cooling are listed in Table 3.

Step IV: Annealing

The annealing step involves allowing the slurry to remain at the final temperature of the controlled cooling step for a designated amount of time. This step is performed to ensure that the slurry freezes completely or substantially completely. The preferred parameters for annealing are listed in Table 4.

Step V: Sublimation

The sublimation step comprises reducing, while the frozen slurry is maintained at roughly the final temperature of the controlled cooling and annealing steps, the pressure in the environment around the mould and frozen slurry to below the triple point of the water/ice/water vapour system, followed by elevation of the temperature to greater than the temperature of the solid-vapor transition temperature at the achieved vacuum pressure (typically $\geq 0°$ C.). This step is performed to remove the ice crystals from the frozen slurry via sublimation. The advantage of sublimation over evaporation as a means of water removal is that it leaves a network of empty space (i.e. pores) that mimics precisely the architecture of the previously existing network of ice crystals. If the ice is allowed to melt, the ice crystal network loses its shape, and the architecture of the resulting pore network is compromised. Preferred parameters for the sublimation step are shown in Table 5.

Step V+I: Crosslinking

If desired, the process may also involve a crosslinking step to crosslink the collagen and the glycosaminoglycan. This is described in the applicant's earlier patent application, PCT/GB04/004550, filed 28 Oct. 2004. The content of PCT/GB04/004550 is incorporated herein by reference.

EXAMPLES

Example I

Single-Layer Scaffold of Collagen/GAG/CaP

Materials

Collagen: Type I, microfibrillar collagen from bovine tendon, Integra Life Sciences Plainsboro, N.J., USA GAG: Chondroitin-6-sulphate from shark cartilage, sodium salt, Sigma-Aldrich Inc (St. Louis, Mo., USA)

Calcium Sources: (i) Calcium hydroxide ($Ca(OH)_2$), Sigma-Aldrich Inc (St. Louis, Mo., USA); (ii) Calcium nitrate ($Ca(NO_3)_2.4H_2O$), Sigma-Aldrich Inc (St. Louis, Mo., USA)

Phosphorous Source: Orthophosphoric acid ($H_3PO_4$), BDH Laboratory Supplies (Poole, United Kingdom)

Crosslinking Agents: 1-Ethyl-3-(3-Dimethylaminopropyl) Carbodiimide (=EDAC), Sigma-Aldrich Inc (St. Louis, Mo., USA); N-Hydroxysuccinimide (=NHS), Sigma-Aldrich Inc (St. Louis, Mo., USA)

Procedure

Step 0: Slurry Preparation 3.8644 g collagen was dispersed in 171.4 mL of 0.1383M $H_3PO_4$ cooled in an ice bath by blending for 90 minutes at 15,000 rpm using a homogeniser equipped with a 19 mm diameter stator to create a highly viscous collagen dispersion. In parallel, 0.3436 g chondroitin-6-sulphate (GAG) was allowed to dissolve in 14.3 mL of 0.1383M $H_3PO_4$ at room temperature by shaking periodically to disperse dissolving GAG in order to produce a GAG solution. After 90 minutes, the 14.3 mL of GAG solution was added to the mixing collagen dispersion at a rate of approximately 0.5 mL/min under continuous homogenisation at 15,000 rpm, and the resulting highly-viscous collagen/GAG dispersion blended for an additional 90 minutes. After 90 minutes of mixing, 1.804 g $Ca(OH)_2$ and 0.780 g $Ca(NO_3)_2.4H_2O$ were added to the highly-viscous collagen/GAG dispersion over 30 minutes under constant blending at 15,000 rpm, creating a collagen/GAG/CaP slurry, the pH of which was approximately 4.0. The collagen/GAG/CaP slurry was allowed to remain at 25°

C. for a period of 48 hours mixing on a stir plate, and was then placed at 4° C. for a subsequent 12 hours. The chilled slurry was then degassed in a vacuum flask over 25 hours at a pressure of 25 Pa.

Step I: Casting 15 mL of the mineralised collagen/GAG/CaP slurry was cast into a polysulphone mould, 50 mm long by 30 mm wide by 10 mm deep, using an auto-pipettor. All large bubbles were removed from the slurry using a hand pipettor.

Step II: Inter-Diffusion

As the scaffold for Example I comprised only one layer, the inter-diffusion step was unnecessary.

Step III: Controlled Cooling

The mould and slurry were placed in a VirTis Genesis freeze dryer (equipped with temperature-controlled, stainless steel shelves) and the shelf temperature of the freeze dryer ramped from 4° C. to −20° C. at a rate of approximately 2.4° C. per minute.

Step IV: Annealing

The shelf temperature of the freeze dryer was maintained at −20° C. for 10 hours.

Step V: Sublimation

While still at a shelf temperature of −20° C., a vacuum of below 25 Pa (approximately 200 mTorr) was applied to the chamber containing the mould and the (now frozen) slurry. The temperature of the chamber was then raised to 37° C., and sublimation allowed to continue for 36 hours. The vacuum was then removed, and the temperature returned to room temperature, leaving a single-layered scaffold of collagen/GAG/CaP, 50 mm by 30 mm by 10 mm in size.

Step V+I: Crosslinking

Scaffolds were hydrated in 40 mL deionised water for 20 minutes. 20 mL of a solution of 0.035M EDAC and 0.014M NHS was added to the container containing the scaffolds and deionised water, and the scaffolds were allowed to crosslink for 2 hours at room temperature under gentle agitation. The EDAC solution was removed, and the scaffolds were rinsed with phosphate buffer solution (PBS) and then allowed to incubate at 37° C. for 2 hours in fresh PBS under mild agitation. After two hours in PBS, the scaffolds were rinsed by allowing them to incubate in deionised water for two ten-minute intervals at 37° C. under mild agitation. The scaffolds were then freeze-dried to remove any residual water by controlled cooling from room temperature to −20° C. at a rate of approximately 2.4° C. per minute, followed by annealing at −20° C. for approximately 5 hours, and then sublimation at below 25 Pa at 37° C., resulting in a crosslinked collagen/GAG/CaP scaffold roughly 50 mm by 30 mm by 10 mm in size.

X-ray microtomographic images, scanning electron microscope images, ion distribution maps and compressive mechanical behaviour of the resulting one-layer scaffolds have been undertaken. Of note in relation to X-ray microtomography is the substantially uniform nature of both material composition and porosity throughout the scaffold. Sequential cross-sections of the same scaffold illustrate the uniform nature of the scaffold pore structure; also evident is the high degree of pore interconnectivity, the equiaxed pore morphology and the large (mean diameter of 500 microns) macropore size. SEM micrographs again show the macropore morphology while also showing the presence of limited microporosity, visible within the walls of certain macropores. High (4000.times.) magnification secondary (i.e. topography-sensitive) and backscattered (i.e. composition-sensitive) electron images of a region of the scaffold wall demonstrate the compositional homogeneity of the scaffold walls, despite the presence of limited topological variations in the form of protruding nodules approximately 1-2 microns in size. Calcium and phosphorous maps corroborate the conclusion of substantially compositional homogeneity throughout the scaffold, with both elements distributed evenly throughout the scaffold. Single-layered scaffolds in the dry state have the ability to be cut to any desired shape without crumbling, cracking or losing their integrity using common surgical tools such as scalpels, razor blades and trephine blades (circular cutting tools used during corneal transplantation). The behaviour of single-layered scaffolds in the dry state exhibits the three-stages of deformation typical of porous solids, with an elastic modulus of 762+/−188 kPa and a compressive yield stress of 85.2+/−11.7 kPa. It is significant to note that the yield strength of the dry scaffolds allows them to withstand firm thumb pressure (during insertion into a defect site, for example) without deforming permanently yet still be formed when strong thumb pressure is applied (by a surgeon modifying the shape of the implant, for example). The compressive deformation of single-layered scaffolds in the hydrated state exhibit three-stage mechanical behaviour under compressive loading, but with elastic modulus (4.12+/−0.76 kPa) and yield stress (0.29+/−0.11 kPa) roughly an order of magnitude lower than the corresponding properties of dry scaffolds. Furthermore, evidence of viscoelastic strain recovery has been observed following release of compressive stresses in the collapse plateau region.

Example II

Two-Layer Mineralised-Unmineralised Scaffold

Materials

Collagen (for mineralised slurry): Type I microfibrillar collagen from bovine tendon, Integra Life Sciences Plainsboro, N.J., USA GAG (for mineralised slurry): Chondroitin-6-sulphate from shark cartilage, sodium salt, Sigma-Aldrich Inc (St. Louis, Mo., USA)

Type II Collagen

+GAG (for unmineralised slurry): Type II Collagen and GAG (Collagen/GAG) slurry solubilised from porcine cartilage, Gelstlich Biomaterials (Wolhusen, Switzerland).

Calcium Sources: (i) Calcium hydroxide ($Ca(OH)_2$) Sigma-Aldrich Inc (St. Louis, Mo., USA); (ii) Calcium nitrate, $Ca(NO_3)_2.4H_2O$, Sigma-Aldrich Inc (St. Louis, Mo., USA)

Phosphorous Source: Orthophosphoric acid ($H_3PO_4$), BDH Laboratory Supplies (Poole, United Kingdom)

Crosslinking Agents: 1-Ethyl-3-(3-Dimethylaminopropyl) Carbodiimide (=EDAC), Sigma-Aldrich Inc (St. Louis, Mo., USA); N-Hydroxysuccinimide (=NHS), Sigma-Aldrich Inc (St. Louis, Mo., USA)

Step 0: Slurry Preparation

Mineralised Slurry Preparation 3.8644 g collagen was dispersed in 171.4 mL of 0.1383M $H_3PO_4$ cooled in an ice bath by blending for 90 minutes at 15,000 rpm using a homogeniser equipped with a 19 mm diameter stator to create a highly viscous collagen dispersion. In parallel, 0.3436 g chondroitin-6-sulphate (GAG) was allowed to dissolve in 14.3 mL of 0.1383M $H_3PO_4$ at room temperature by shaking periodically to disperse dissolving GAG in order to produce a GAG solution. After 90 minutes, the 14.3 mL of GAG solution was added to the mixing collagen dispersion at a rate of approximately 0.5 mL/min, under continuous homogenisation at 15,000 rpm, and the resulting highly-viscous collagen/GAG dispersion blended for an additional 90 minutes. After 90 minutes of mixing, 1.804 g Ca(OH)$_2$ and 0.780 g Ca(NO$_3$)$_2$.4H$_2$O were added to the highly-viscous collagen/GAG dispersion over 30 minutes under constant blending at 15,000 rpm, creating a collagen/GAG/CaP slurry, the pH of which was approximately 4.0. The chilled slurry was then degassed in a vacuum flask over 25 hours at a pressure of 25 Pa, reblended using the homogenizer over 30 minutes, and then degassed again for 48 hours.

Unmineralised Slurry Preparation

Type II collagen/GAG slurry was removed from refrigerator and allowed to return to room temperature.

Step I: Casting 2.5 mL of the unmineralised Type II collagen/GAG slurry was placed in the bottom portion of a combination polysulphone mould, the bottom portion of which measured 50 mm in length by 30 mm in width by 2 mm in depth. The slurry was smoothed to a flat surface using a razor blade. An upper collar, also made of polysulphone, and measuring 50 mm in length by 30 mm in width by 6 mm in depth, was attached to the bottom portion of the mould containing the smoothed, unmineralised slurry. 9 mL of the mineralised collagen/GAG/CaP slurry was placed, in an evenly distributed manner, on top of the smoothed, unmineralised layer and within the previously empty upper collar. All large bubbles were removed from the slurry using a hand pipettor.

Step II: Inter-Diffusion

The layered slurry was allowed to remain at room temperature and pressure for a total of 4 hours, before being placed in the freeze dryer.

Step III: Controlled Cooling

The mould and layered slurry were placed in a VirTis Genesis freeze dryer (equipped with temperature-controlled, stainless steel shelves) and the shelf temperature of the freeze dryer ramped from 4° C. to −40° C. at a rate of approximately −2.4° C. per minute.

Step IV: Annealing

The shelf temperature of the freeze dryer was maintained at −40° C. for 10 hours.

Step V: Sublimation

While still at a shelf temperature of −40° C., a vacuum of below 25 Pa (approximately 200 mTorr) was applied to the chamber containing the mould and the (now frozen) layered slurry. The temperature of the chamber was then raised to 37° C., and sublimation allowed to continue for 36 hours. The vacuum was then removed, and the temperature returned to room temperature, leaving a two-layered scaffold of collagen/GAG/CaP, 50 mm by 30 mm by 8 mm in size, comprised of an unmineralised layer 2 mm thick, and a mineralised layer 6 mm thick.

Step V+I: Crosslinking

Scaffolds were hydrated in 32 mL deionised water for 20 minutes. 18 mL of a solution of 0.035M EDAC and 0.014M NHS was added to the container containing the scaffolds and deionised water, and the scaffolds were allowed to crosslink for 2 hours at room temperature under gentle agitation. The EDAC solution was removed and the scaffolds were then rinsed with phosphate buffer solution (PBS) and then allowed to incubate at 37° C. for 2 hours in fresh PBS under mild agitation. After two hours in PBS, the scaffolds were rinsed by allowing them to incubate in deionised water for two 10-minute intervals at 37° C. under mild agitation. The scaffolds were then freeze-dried to remove any residual water by controlled cooling from room temperature to −20° C. at a rate of approximately −2.4° C. per minute, followed by annealing at −20° C. for 5 hours, and finally by sublimation at below 25 Pa at 37° C. for 24 hours, resulting in a crosslinked, layered collagen/GAG/CaP scaffold roughly 50 mm by 30 mm by 8 mm in size, comprised of an unmineralised layer 2 mm thick, and a mineralised layer 6 mm thick.

X-ray microtomographic images, scanning electron microscope images, and ion distribution maps of the resulting two-layer scaffolds have been undertaken. An x-ray microtomographic image of a 9.5 mm.times.9.5 mm cylindrical section of the two-layer scaffold produced by the procedure described above includes an opaque lower region that shows the mineralised layer, while a more translucent upper region represents the unmineralised layer. Both layers are largely uniform, both in terms of porosity and composition. The mean macropore size in the mineralised layer is approximately 400 microns, while that in the unmineralised layer is on the order of 700 microns; the pores in both mineralised and unmineralised layers exhibit an equiaxed morphology. A SEM image shows a top view of the unmineralised layer, illustrating that little evidence of microporosity is present, while images of the interface region demonstrate the lack of any large voids or other discontinuities separating the mineralised and unmineralised layers. The behaviour of two-layered scaffolds under compressive loading has been investigated. Upon application of compressive load, the compliant unmineralised layer begins to compress, resulting in near-complete compaction of the cartilaginous compartment at stresses insufficient to induce any significant deformation in mineralised scaffolds. After the load is released, the unmineralised collagen/GAG layer returns to its original shape almost instantaneously. The mechanical behaviour of two-layered scaffolds in the hydrated state has been investigated. Once hydrated, the unmineralised collagen/GAG layer can be compressed under low-magnitude loads. Unlike in the dry state, the hydrated unmineralised compartment does not fully regain its original thickness after the first application of compressive load, but instead drapes over the cross section of the mineralised compartment. After this initial compression, however, the unmineralised layer returns to its compressed thickness after each subsequent application of compressive load. The ability of the unmineralised layer of a two-layer scaffold to adhere to the walls of a surgical defect encompassing the bone and cartilage interface in articular joints has been investigated. A glass slide is analogous to the wall of an osteochondral defect, and the ability of the unmineralised layer to adhere to this surface illustrates the capacity of these scaffolds to fill such defects to their periphery without the persistence of gaps between the unmineralised layer of the scaffold and the adjacent articular cartilage.

Example III

Three Layer Mineralised-Unmineralised Mineralised Scaffold

Materials

Collagen (for mineralised slurry): Type I microfibrillar collagen from bovine tendon, Integra Life Sciences (Plainsboro, N.J., USA)

GAG (for mineralised slurry): Chondroitin-6-sulphate from shark cartilage, sodium salt, Sigma-Aldrich Inc (St. Louis, Mo., USA)

Calcium Sources: (i) Calcium hydroxide (Ca(OH)$_2$), Sigma-Aldrich Inc (St. Louis, Mo., USA); (ii) Calcium nitrate (Ca(NO$_3$)$_2$.4H$_2$O), Sigma-Aldrich Inc (St. Louis, Mo., USA)

Phosphorous Source: Orthophosphoric acid (H$_3$PO$_4$), BDH Laboratory Supplies (Poole, United Kingdom)

Collagen (for unmineralised collagen-GAG slurry): 85% Type I, 15% Type III Pepsin solubilised from porcine dermis, Japan Meat Packers (Osaka, Japan)

GAG (for unmineralised slurry): Chondroitin-6-sulphate from shark cartilage, sodium salt, Sigma-Aldrich Inc (St. Louis, Mo., USA)

Diluents for unmineralised Collagen and GAG: Glacial acetic acid ($CH_3COOH$), Fischer Scientific (Loughborough, UK)

Crosslinking Agents: Nordihydroguariaretic acid (NDGA), Sigma-Aldrich Inc (St. Louis, Mo., USA);

Sodium dihydrogen phosphate ($NaH_2PO_4$), BDH Laboratory Supplies (Poole, United Kingdom)

Sodium chloride (NaCl), Sigma-Aldrich Inc (St. Louis, Mo., USA)

Step 0: Slurry Preparation

Mineralised Slurry Preparation 3.8644 g collagen was dispersed in 171.4 mL of 0.1383M $H_3PO_4$ cooled in an ice bath by blending for 90 minutes at 15,000 rpm, using a homogeniser equipped with a 19 mm diameter stator to create a highly viscous collagen dispersion. In parallel, 0.3436 g chondroitin-6-sulphate (GAG) allowed to dissolve in 14.3 mL of 0.1383M $H_3PO_4$ at room temperature by shaking periodically to disperse dissolving GAG in order to produce a GAG solution. After 90 minutes, the 14.3 mL of GAG solution was added to the mixing collagen dispersion at a rate of approximately 0.5 mL/min, under continuous homogenisation at 15,000 rpm, and the resulting highly-viscous collagen/GAG dispersion blended for an additional 90 minutes. After 90 minutes of mixing, 1.804 g $Ca(OH)_2$ and 0.780 g $Ca(NO_3)_2 \cdot 4H_2O$ were added to the highly-viscous collagen/GAG dispersion over 30 minutes under constant blending at 15,000 rpm, creating a collagen/GAG/CaP slurry, the pH of which was approximately 4.0. The chilled slurry was then degassed in a vacuum flask over 25 hours at a pressure of 25 Pa, reblended using the homogenizer over 30 minutes, then degassed again for 48 hours.

Unmineralised Slurry Preparation 1.9322 g of the Type I/III collagen was dispersed in 171.4 mL of 0.05M acetic acid cooled in an ice bath by blending for 90 minutes at 15,000 rpm, using a homogeniser equipped with a 19 mm diameter stator in order to create a highly viscous collagen dispersion. In parallel, 0.1718 g chondroitin-6-sulphate (GAG) was allowed to dissolve in 28.6 mL of 0.05M acetic acid at room temperature, by shaking periodically to disperse dissolving GAG in order to produce a GAG solution. After 90 minutes, the 14.3 mL of GAG solution was added to the mixing collagen dispersion at a rate of approximately 0.5 mL/min, under continuous homogenisation at 15,000 rpm, and the resulting highly-viscous collagen/GAG dispersion blended for an additional 90 minutes.

Step I: Casting 3.5 mL of the mineralised collagen/GAG/CaP slurry was placed in the bottom portion of a combination polysulphone mould, the bottom portion of which measured 50 mm in length by 30 mm in width by 3 mm in depth. The slurry was smoothed to a flat surface using a razor blade. A middle collar, also made of polysulphone, and measuring 50 mm in length by 30 mm in width by 5 mm in depth, was attached to the bottom portion of the mould containing the smoothed, mineralised slurry. 7.5 mL of the unmineralised collagen/GAG slurry was placed, in an evenly distributed manner, on top of the smoothed, unmineralised layer and within the previously empty middle collar. An upper collar, also made of polysulphone and measuring 50 mm in length by 30 mm in width by 3 mm in depth, was attached to the middle portion of the mould above the smoothed, unmineralised slurry. 3.5 mL of the mineralised collagen/GAG/CaP slurry was placed, in an evenly distributed manner, on top of the smoothed, unmineralised layer and within the previously empty upper collar. All large bubbles were removed from the slurry using a hand pipettor.

Step II: Inter-Diffusion

The three-layer slurry was allowed to remain at room temperature and pressure for 20 minutes before being placed in the freeze dryer.

Step III: Controlled Cooling

The mould and three-layer slurry were placed in a VirTis AdVantage freeze dryer (equipped with temperature-controlled, stainless steel shelves) and the shelf temperature of the freeze dryer ramped from 4° C. to −40° C. at a rate of approximately −2.4° C. per minute.

Step IV: Annealing

The shelf temperature of the freeze dryer was maintained at −40° C. for 10 hours.

Step V: Sublimation

While still at a shelf temperature of −40° C., a vacuum of below 25 Pa (approximately 200 mTorr) was applied to the chamber containing the mould and the (now frozen) three-layer slurry. The temperature of the chamber was then raised to 37° C., and sublimation allowed to continue for 36 hours. The vacuum was then removed, and the temperature returned to room temperature, leaving a three-layered scaffold 50 mm by 30 mm by 11 mm in size, comprised of an unmineralised middle layer 5 mm thick, surrounded by two mineralised layers 3 mm thick.

Step VI: Crosslinking

The three-layer scaffold was hydrated in 0.1M NaH2PO4 and 0.15M NaCl in phosphate buffered saline (PBS; pH 7.0) for 30 minutes. NDGA was suspended in 1N NaOH and added to PBS to produce a 3 mg/mL solution of NGDA in PBS; scaffolds were then hydrated in this solution under agitation for 24 hours. The three-layer scaffold was removed from the NGDA-PBS solutions and rinsed with deionised water. The scaffolds were then freeze-dried to remove any residual water by controlled cooling from room temperature to −20° C. at a rate of approximately 2.4° C. per minute, followed by annealing at −20° C. for 5 hours, and finally sublimation at below 25 Pa at 37° C. for 24 hours, resulting in a dry, crosslinked scaffold. A subsequent treatment was then performed at a concentration of 0.1 mg/mL NDGA. The scaffolds were then washed in 70% ethanol for 6 hours and subsequently washed for 24 hours in PBS at room temperature. The scaffolds were then freeze dried for a second time to remove any residual water by controlled cooling from room temperature to −20° C. at a rate of approximately 2.4° C. per minute, followed by annealing at −20° C. for 5 hours, and finally sublimation at below 25 Pa at 37° C. for 24 hours.

The parameters in the Tables below are applicable singularly or in combination to any aspect of the present invention unless otherwise stated.

TABLE 1

Preferred Parameters for Casting

| | | |
|---|---|---|
| Starting Temperature for Controlled Cooling | Preferable | 0 to 37° C. |
| | More Preferable | 2 to 37° C. |
| | Most Preferable | 4 to 37° C. |
| Layer Thickness | Preferable | 0.1-500 mm |
| | More Preferable | 0.5-20 mm |
| | Most Preferable | 1.0-10 mm |
| Slurry Viscosity | Preferable | 0.1-50 Pa · s |
| | More Preferable | 0.1-10 Pa · s |
| | Most Preferable | 0.5-5 Pa · s |

TABLE 1-continued

Preferred Parameters for Casting

| | | | |
|---|---|---|---|
| Thickness of Mould Walls | Preferable | 1-50 | mm |
| | More Preferable | 5-20 | mm |
| | Most Preferable | 5-15 | mm |
| Number of Layers | Preferable | 1-50 | |
| | More Preferable | 1-5 | |
| | Most Preferable | 1-3 | |

TABLE 2

Preferred Parameters for Inter-diffusion

| | | | |
|---|---|---|---|
| Time Allowed for Inter-diffusion | Preferable | 0-24 | hours |
| | More Preferable | 0-6 | hours |
| | Most Preferable | 0-2 | hours |
| Temperature | Preferable | 2-40° | C. |
| | More Preferable | 4-37° | C. |
| | Most Preferable | 20-37° | C. |
| Pressure | Preferable | 1-200 | kPa |
| | More Preferable | 50-150 | kPa |
| | Most Preferable | 50-101.325 | kPa |

TABLE 3

Preferred Parameters for Controlled Cooling

| | | | |
|---|---|---|---|
| Cooling Rate | Preferable | 0.02-10.0° | C./min |
| | More Preferable | 0.02-6.0° | C./min |
| | Most Preferable | 0.2-2.7° | C./min |
| Final Cooling Temperature | Preferable | −100 to 0° | C. |
| | More Preferable | −80 to −10° | C. |
| | Most Preferable | −40 to −20° | C. |

TABLE 4

Preferred Parameters for Annealing

| | | | |
|---|---|---|---|
| Annealing Temperature | Preferable | −100 to 0° | C. |
| | More Preferable | −80 to −10° | C. |
| | Most Preferable | −40 to −20° | C. |
| Annealing Time | Preferable | 0-48 | hours |
| | More Preferable | 2-12 | hours |
| | Most Preferable | 8-10 | hours |

TABLE 5

Preferred Parameters for Sublimation

| | | | |
|---|---|---|---|
| Sublimation Pressure | Preferable | 0-0.08 | kPa |
| | More Preferable | 0.0025-0.08 | kPa |
| | Most Preferable | 0.0025-0.04 | kPa |
| Sublimation Time | Preferable | 0-120 | hours |
| | More Preferable | 12-72 | hours |
| | Most Preferable | 24-36 | hours |
| Sublimation Temperature | Preferable | −10-60° | C. |
| | More Preferable | 0-40° | C. |
| | Most Preferable | 20-37° | C. |

REFERENCES

Gao J, Dennis J E, Solchaga L A, Awadallah A S, Goldberg V M, Caplan A I. 2001. Tissue-Engineered Fabrication of an Osteochondral Composite Graft Using Rat Bone Marrow-Derived Mesenchymal Stem Cells. Tissue Engineering 7:363-371.

Gao J, Dennis J E, Solchaga L A, Goldberg V M, Caplan A I. 2002. Repair of Osteochondral Defect with Tissue-Engineered Two-Phase Composite Material of Injectable Calcium Phosphate and Hyaluronan Sponge. Tissue Engineering 8:827-837.

Hung C T, Lima E G, Mauck R L, Taki E, LeRoux M A, Lu H H, Stark R G, Guo X E, Ateshian G A. 2003. Anatomically Shaped Osteochondral Constructs for Articular Cartilage Repair. Journal of Biomechanics 36:1853-1864.

Hunziker E B, Driesang I M K. 2003. Functional Barrier Principle for Growth-Factor-Based Articular Cartilage Repair. Osteoarthritis and Cartilage 11:320-327.

Niederauer G G, Slivka M A, Leatherbury N C, Korvick D L, H. H. H J, Ehler W C, Dunn C J, Kieswetter K. 2000. Evaluation of Multiphase Implants for Repair of Focal Osteochondral Defects in Goats. Biomaterials 21:2561-2574.

O'Brien F J, Harley B A, Yannas I V, Gibson L. 2004. Influence of Freezing Rate on Pore Structure in Freeze-Dried Collagen-GAG Scaffolds. Biomaterials 25:1077-1086.

O'Brien F J, Harley B A, Yannas I V, Gibson L J. 2005. The Effect of Pore Size and Structure on Cell Adhesion in Collagen-GAG Scaffolds. Biomaterials 26:433-441.

H M Loree, I V Yannas, B Mikic, A S Chang, S M Perutz, T V Norregaard, and C Kararup, 'A freeze-drying process for fabrication of polymeric bridges for peripheral nerve regeneration' Proc. 15th Annual Northeast Bioeng. Conf. P. 53-54, 1989.

Schaefer D, Martin I, Jundt G, Seidel J, Heberer M, Grodzinsky A, Bergin I, Vunjak-Novakovic G, Freed L E. 2002. Tissue-Engineered Composites for the Repair of Large Osteochondral Defects. Arthritis and Rheumatism 46:2524-2534.

Schaefer D, Martin I, Shastri P, Padera R F, Langer R, Freed L E, Vunjak-Novakovic G. 2000. In Vitro Generation of Osteochondral Composites. Biomaterials 21:2599-2606.

Sherwood J K, Riley S L, Palazzolo R, Brown S C, Monkhouse D C, Coates M, Griffith L G, Landeen L K, Ratcliffe A. 2002. A Three-Dimensional Osteochondral Composite Scaffold for Articular Cartilage Repair. Biomaterials 23:4739-4751.

Yannas I V, Lee E, Orgill D P, Skrabut E M, Murphy G F. 1989. Synthesis and Characterization of a Model Extracellular Matrix that Induces Partial Regeneration of Adult Mammalian Skin. Proceedings of the National Academy of Sciences of the United States of America 86:933-937.

The present invention finds application in a number of areas and the following are provided by way of example.

Articular Cartilage Repair Product: Two-Layer Scaffold

Two layer scaffolds hold the potential to enhance the efficacy of existing first-line surgical procedures that recruit marrow-derived stem cells to the site of articular-cartilage injury. Delivered as, for example, a dry, 2 cm×2 cm×1 cm block of dry, vacuum-packed, gamma-sterilised material resembling styrofoam, these scaffolds can be cut using a scalpel or other tools, are easily inserted into the defect using simple thumb- or blunt-instrument pressure, and bond directly to the site without sutures or glue.

Patellar Ligament Donor-Site Repair Product: Three Layer Scaffolds

Three-layer scaffolds hold the potential to enhance regeneration at patellar ligament (patella tendon) donor sites during anterior cruciate ligament (ACL) reconstruction, reducing frontal knee pain and reducing the risk of patellar ligament rupture and patellar fracture.

Tendon Repair Product: Two-Layer Scaffolds

Two-layer scaffolds with extended unmineralised components hold the potential to improve the efficacy of tendon repair during rotator-cuff procedures and to address small-tendon applications for which no effective solution currently exists.

The present invention has been further studied on the basis of large-animal trials and a summary is presented below.

Trial 1: Ovine Bone Defect Model

The present invention enables the production of layered tissue regeneration scaffolds whose structure and composition mimic bone on one side, unmineralised tissue (e.g. cartilage, ligament, tendon) on the other side, and a smooth, stable interface in between. The present invention furthermore offers the capacity to systematically alter the chemical composition of the mineral phase of the bony compartment of such implants.

Animal: skeletally mature Texcel Continental sheep (female).

Defect: 9 mm diameter by 9 mm deep cancellous bone defect on lateral femoral condyle.

Implantation Period: 6 weeks.

Experimental Groups: Six implants of each experimental group implanted contralaterally with the same implant type in each side of the same animal.

Control Groups:

Positive Control: four sites were filled with cancellous autograft harvested from the tibial tuberosity.

Negative Control: four sites were filled with control implants comprising implants containing no mineral phase at all (i.e. containing the organic constituents of the bony side of ChondroMimetic only).

Study Objective: to identify differences in the performance of four experimental implant groups differentiated by chemical composition and to identify the most desirable of these as the final composition for the bone compartment of Chondro-Mimetic.

Significant Findings: none of the three experimental groups invoked adverse immune responses of any kind; all three experimental groups plus the unmineralised negative control group supported bony in-growth via a cell-mediated direct substitution mechanism; no statistically significant differences between there three implant groups were observed; and bone formation observed in all three experimental groups was higher than that in the negative control group to a statistically significant level.

Implications for Implant Design: The direct substitution mechanism implied by this study suggests that the bone formation mechanism more closely resembles the templated bone formation that occurs at the growth plate in foetal and neonatal animals (including humans) than the typical apposition mechanism observed in traditional bone-graft substitutes. The presence of this substitution mechanism in the unmineralised control suggests that it is the organic constituent of the implants that imparts this character.

Pore size for the implants should be altered to account for this substitution mechanism by reducing the mean pore size of the bony compartment of the implants.

Lack of statistically significant differences in the bone formation behaviour of the three experimental groups suggests that processing parameters may be used to identify the most appropriate mineral composition of the implants.

Trial 2: Caprine Osteochondral Defect Model

The objective of this study was to evaluate the performance of ChondroMimetic as a means of improving the results of a marrow stimulation technique (subchondral drilling).

Animal: skeletally mature Spanish goats (female).

Defect: 4 mm diameter by 6 mm deep osteochondral defects (1 in trochlear groove; 1 on the lateral condyle).

Implantation Period: 16 weeks.

Experimental Groups: Six implants of the ChondroMimetic working prototype.

Control Group: Six defects simulating traditional subchondral drilling (i.e. containing no implants).

Study Objective: to evaluate the performance of Chondro-Mimetic as an aid to marrow stimulatio Findings: feedback from surgeons about the handling characteristics of ChondroMimetic was, without exception, overwhelmingly positive.

The invention claimed is:

1. A process for the preparation of a composite biomaterial comprising:
   providing a first substantially solid component comprising one or more of collagen, a glycosaminoglycan, albumin, hyaluronan, chitosan, and synthetic polypeptides comprising a portion of the polypeptide sequence of collagen, and optionally an inorganic material, said component having at least a surface portion that is porous;
   providing a fluid composition comprising one or more of collagen, a glycosaminoglycan, albumin, hyaluronan, chitosan, and synthetic polypeptides comprising a portion of the polypeptide sequence of collagen, and a liquid carrier, and optionally an inorganic material;
   contacting said fluid composition with said porous surface portion of said first component;
   cooling said fluid composition to a temperature at which the liquid carrier transforms into a plurality of solid crystals or particles;
   removing at least some of the plurality of solid crystals or particles by sublimation and/or evaporation;
   wherein said cooling said fluid composition yields a second component, and wherein the first and/or the second component comprise said inorganic material and said inorganic material is calcium phosphate.

2. A process for the preparation of a composite biomaterial comprising:
   providing a first substantially solid component comprising one or more of collagen, a glycosaminoglycan, albumin, hyaluronan, chitosan, and synthetic polypeptides comprising a portion of the polypeptide sequence of collagen, and optionally an inorganic material, said component having at least a surface portion that is porous;
   providing a fluid composition comprising one or more of collagen, a glycosaminoglycan, albumin, hyaluronan, chitosan, and synthetic polypeptides comprising a portion of the polypeptide sequence of collagen, and a liquid carrier, and optionally an inorganic material;
   providing a second substantially solid component comprising one or more of collagen, a glycosaminoglycan, albumin, hyaluronan, chitosan, and synthetic polypeptides comprising a portion of the polypeptide sequence of collagen, and optionally an inorganic material, said component having at least a surface portion that is porous;
   interposing said fluid composition between said first and second components so that it contacts with said porous surface portions;
   cooling said fluid composition between said first and second components to a temperature at which the liquid carrier transforms into a plurality of solid crystals or particles;
   removing at least some of the plurality of solid crystals or particles by sublimation and/or evaporation, to result in an intermediate layer between the first and second components.

3. A process as claimed in claim 1, wherein the calcium phosphate material comprises one or more of brushite, octa-calcium phosphate and apatite.

4. A process as claimed in claim 1, wherein said cooling said fluid composition yields a second substantially solid component, and wherein the first component and/or the second component comprise (s) collagen and optionally a glycosaminoglycan.

5. A process as claimed in claim 1, wherein said cooling said fluid composition yields a second substantially solid component, and wherein the first component and/or the second component is/are formed from a co-precipitate of collagen and a calcium phosphate material.

6. A process as claimed in claim 1, wherein said cooling said fluid composition yields a second substantially solid component, and wherein the first component and/or the second component is/are formed from a co-precipitate of collagen and a glycosaminoglycan.

7. A process as claimed in claim 1, wherein said cooling said fluid composition yields a second substantially solid component, and wherein the first component and/or the second component is/are formed a triple co-precipitate of collagen, a calcium phosphate material and a glycosaminoglycan.

8. A process as claimed in claim 2, wherein the first component comprises collagen and a glycosaminoglycan and optionally a calcium phosphate material, and wherein the second component comprises collagen, a glycosaminoglycan and a calcium phosphate material.

9. A process as claimed in claim 1, wherein the fluid composition comprises an inorganic material.

10. A process as claimed in claim 9, wherein the inorganic material comprises a calcium phosphate material.

11. A process as claimed in claim 10, wherein the calcium phosphate material comprises one or more of brushite, octa-calcium phosphate and apatite.

12. A process as claimed in claim 1, wherein the fluid composition comprises collagen and optionally a glycosaminoglycan.

13. A process as claimed in claim 1, wherein the liquid carrier comprises water.

14. A process as claimed in claim 1, wherein the fluid composition is provided in the form of a suspension.

15. A process as claimed in claim 14, wherein the fluid composition comprises a collagen-based suspension.

16. A process as claimed in claim 1, wherein the fluid composition is provided in the form of a slurry.

17. A process as claimed in claim 16, wherein the fluid composition is a slurry comprising collagen and optionally a glycosaminoglycan and optionally a calcium phosphate material.

18. A process as claimed in claim 17, wherein the fluid composition is a slurry comprising a co-precipitate of collagen and a glycosaminoglycan.

19. A process as claimed in claim 17, wherein the fluid composition is a slurry comprising a triple co-precipitate of collagen, a calcium phosphate material and a glycosaminoglycan.

20. A process as claimed in claim 1, wherein the composite biomaterial is a multilayer scaffold.

21. A process as claimed in claim 2, wherein the composition of the first component is not the same as the composition of the second component.

22. A process as claimed in claim 2, wherein the composition of the fluid component is not the same as the composition of the first component or the second component.

23. A process as claimed in claim 1 wherein the porous surface portion has a porosity between 50 and 99.99 vol. %.

24. A process as claimed in claim 1 wherein the porous surface portion has a porosity between 70 and 98 vol. %.

25. A process as claimed in claim 2 wherein the porous surface portion has a porosity between 50 and 99.99 vol. %.

26. A process as claimed in claim 2 wherein the porous surface portion has a porosity between 70 and 98 vol. %.

27. A process as claimed in claim 1 wherein the first substantially solid component comprises said inorganic material.

28. A process as claimed in claim 2 wherein the first and/or the second component comprise (s) an inorganic material.

29. A process as claimed in claim 28, wherein the inorganic material comprises a calcium phosphate material.

30. A process as claimed in claim 29, wherein the calcium phosphate material comprises one or more of brushite, octa-calcium phosphate and apatite.

31. A process as claimed in claim 2, wherein the first component and/or the second component comprise (s) collagen and optionally a glycosaminoglycan.

32. A process as claimed in claim 2, wherein the first component and/or the second component is/are formed from a co-precipitate of collagen and a calcium phosphate material.

33. A process as claimed in claim 2, wherein the first component and/or the second component is/are formed from a co-precipitate of collagen and a glycosaminoglycan.

34. A process as claimed in claim 2, wherein the first component and/or the second component is/are formed a triple co-precipitate of collagen, a calcium phosphate material and a glycosaminoglycan.

35. A process as claimed in claim 1 wherein the first component and the second component are essentially solid.

36. A process as claimed in claim 1 wherein the first component and the second component are solid.

37. A process as claimed in claim 2 wherein the first component and the second component are essentially solid.

38. A process as claimed in claim 2 wherein the first component and the second component are solid.

* * * * *